(12) United States Patent
Bhatia et al.

(10) Patent No.: US 11,054,428 B2
(45) Date of Patent: Jul. 6, 2021

(54) INHALABLE NANOSENSORS WITH VOLATILE REPORTERS AND USES THEREOF

(71) Applicant: Massachusetts Institute of Technology, Cambridge, MA (US)

(72) Inventors: Sangeeta N. Bhatia, Lexington, MA (US); Leslie Wan-Gee Chan, Somerville, MA (US); Melodi Nilgun Anahtar, Cambridge, MA (US); Roderick Russell Kunz, Acton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 91 days.

(21) Appl. No.: 16/293,390

(22) Filed: Mar. 5, 2019

(65) Prior Publication Data
US 2019/0271704 A1 Sep. 5, 2019

Related U.S. Application Data

(60) Provisional application No. 62/638,352, filed on Mar. 5, 2018.

(51) Int. Cl.
*G01N 33/58* (2006.01)
*G01N 33/497* (2006.01)
(Continued)

(52) U.S. Cl.
CPC ............ *G01N 33/587* (2013.01); *C12Q 1/37* (2013.01); *G01N 33/497* (2013.01);
(Continued)

(58) Field of Classification Search
CPC .. C12Q 1/37; G01N 2458/20; G01N 2560/00; G01N 2800/12; G01N 2800/50;
(Continued)

(56) References Cited

U.S. PATENT DOCUMENTS 5,500,161 A 3/1996 Andrianov et al.
5,811,252 A 9/1998 Verheijen
(Continued)

FOREIGN PATENT DOCUMENTS

CN 102558362 A 7/2012
CN 103012595 A 4/2013
(Continued)

OTHER PUBLICATIONS

Zhu et al. Journal of Breath Research, vol. 7(1), Mar. 2013, pp. 1-15.*
(Continued)

*Primary Examiner* — Maureen Wallenhorst
(74) *Attorney, Agent, or Firm* — Wolf, Greenfield & Sacks, P.C.

(57) ABSTRACT

In some aspects, the disclosure relates to compositions and method for detection, classification, and treatment of disease or other body status. The methods and compositions may be methods or compositions for identification of pathogenic infections or other diseases in patients using an inhalable nanosensor having a volatile reporter. The disclosure is based, in part, on synthetic biomarkers (e.g., inhalable nanosensors) that are capable of distinguishing (e.g., classifying) different disease or status associated enzymes in a subject by examining the effect of those enzymes on a synthetic volatile reporter.

28 Claims, 16 Drawing Sheets

Specification includes a Sequence Listing.

(51) Int. Cl.
  *G01N 33/569* (2006.01)
  *G01N 33/543* (2006.01)
  *G01N 33/533* (2006.01)
  *C12Q 1/37* (2006.01)

(52) U.S. Cl.
  CPC ..... *G01N 33/533* (2013.01); *G01N 33/54346* (2013.01); *G01N 33/569* (2013.01); *G01N 33/582* (2013.01); *G01N 2458/20* (2013.01); *G01N 2560/00* (2013.01); *G01N 2800/12* (2013.01); *G01N 2800/50* (2013.01)

(58) Field of Classification Search
  CPC ........... G01N 33/533; G01N 33/54346; G01N 33/569; G01N 33/582; G01N 33/587; G01N 33/497; Y10T 436/19; Y10T 436/24; Y10T 436/25875
  USPC .............. 436/63, 86, 124, 173, 181; 422/84; 435/23, 24, 29, 34
  See application file for complete search history.

(56) References Cited

U.S. PATENT DOCUMENTS

| | | | |
|---|---|---|---|
| 5,885,775 A | 3/1999 | Haff et al. | |
| 6,312,390 B1 | 11/2001 | Phillips | |
| 6,335,429 B1 | 1/2002 | Cai et al. | |
| 6,592,847 B1 | 7/2003 | Weissleder et al. | |
| 6,597,996 B1 | 7/2003 | Venkataraman et al. | |
| 6,629,040 B1 | 9/2003 | Goodlett et al. | |
| 6,824,981 B2 | 11/2004 | Chait et al. | |
| 7,041,453 B2 | 5/2006 | Yang | |
| 7,169,892 B2 | 1/2007 | Atsushi et al. | |
| 7,179,655 B2 | 2/2007 | Patricelli | |
| 7,329,506 B2 | 2/2008 | William | |
| 7,412,332 B1 | 8/2008 | Venkataraman et al. | |
| 7,456,269 B2 | 11/2008 | Gurney et al. | |
| 7,468,258 B2 | 12/2008 | Owen | |
| 7,544,518 B2 | 6/2009 | Aebersold et al. | |
| 7,595,155 B2 | 9/2009 | Murakami | |
| 7,820,108 B2 | 10/2010 | Lampotang et al. | |
| 7,879,574 B2 | 2/2011 | Packard et al. | |
| 7,985,401 B2 | 7/2011 | Jiang et al. | |
| 8,673,267 B2* | 3/2014 | Bhatia ................ | C12Q 1/37 424/9.1 |
| 8,841,085 B2 | 9/2014 | Kwon et al. | |
| 8,969,027 B2 | 3/2015 | Bossmann et al. | |
| 9,006,415 B2 | 4/2015 | Ren et al. | |
| 9,072,792 B2 | 7/2015 | Jiang et al. | |
| 9,657,326 B2* | 5/2017 | Ruether ................. | C12Q 1/04 |
| 9,808,532 B2 | 11/2017 | Tsien et al. | |
| 9,970,941 B2 | 5/2018 | Bhatia et al. | |
| 10,006,916 B2 | 6/2018 | Kwong et al. | |
| 10,527,619 B2 | 1/2020 | Bhatia et al. | |
| 10,883,998 B2 | 1/2021 | Bhatia et al. | |
| 2002/0119490 A1 | 8/2002 | Aebersold et al. | |
| 2004/0014652 A1 | 1/2004 | Dubois et al. | |
| 2004/0091943 A1 | 5/2004 | Schneider | |
| 2005/0107583 A1 | 5/2005 | Jiang et al. | |
| 2005/0260695 A1 | 11/2005 | Fleming et al. | |
| 2006/0008856 A1 | 1/2006 | Singh et al. | |
| 2006/0257883 A1* | 11/2006 | Bjoraker ................ | G01N 33/86 435/6.11 |
| 2006/0292631 A1 | 12/2006 | Broberg et al. | |
| 2007/0010433 A1 | 1/2007 | Albrechtsen et al. | |
| 2007/0048752 A1 | 3/2007 | Yan et al. | |
| 2007/0207555 A1 | 9/2007 | Guerra et al. | |
| 2007/0258894 A1 | 11/2007 | Melker et al. | |
| 2008/0026480 A1 | 1/2008 | Guerra | |
| 2008/0064607 A1 | 3/2008 | Yang | |
| 2008/0095758 A1 | 4/2008 | Lee et al. | |
| 2008/0113875 A1 | 5/2008 | Chaurand et al. | |
| 2008/0213377 A1 | 9/2008 | Bhatia et al. | |
| 2008/0226562 A1 | 9/2008 | Groves et al. | |
| 2008/0241955 A1 | 10/2008 | Purkayastha et al. | |
| 2009/0016988 A1 | 1/2009 | Buckley | |
| 2009/0088332 A1 | 4/2009 | Ju et al. | |
| 2009/0156424 A1 | 6/2009 | Thompson | |
| 2009/0230300 A1 | 9/2009 | Trevejo et al. | |
| 2009/0246142 A1 | 10/2009 | Bhatia et al. | |
| 2010/0022408 A1 | 1/2010 | Singh et al. | |
| 2010/0124757 A1 | 5/2010 | Kwon et al. | |
| 2010/0190193 A1 | 7/2010 | Calatzis et al. | |
| 2010/0240050 A1 | 9/2010 | Bhatia et al. | |
| 2010/0317542 A1 | 12/2010 | Lim et al. | |
| 2011/0014125 A1 | 1/2011 | Bossmann et al. | |
| 2011/0277538 A1 | 11/2011 | Haick | |
| 2012/0183949 A1 | 7/2012 | Hyde et al. | |
| 2013/0078188 A1 | 3/2013 | Tsien et al. | |
| 2013/0295129 A1 | 11/2013 | Irvine et al. | |
| 2013/0315906 A1 | 11/2013 | Lowman et al. | |
| 2014/0234431 A1 | 8/2014 | Bhatia et al. | |
| 2014/0255313 A1 | 9/2014 | Vasiljeva et al. | |
| 2014/0303014 A1 | 10/2014 | Kwong et al. | |
| 2014/0363833 A1* | 12/2014 | Bhatia ............... | G01N 33/54306 435/7.94 |
| 2014/0364368 A1 | 12/2014 | Lin et al. | |
| 2015/0165062 A1 | 6/2015 | Liao et al. | |
| 2016/0289324 A1 | 10/2016 | Moore et al. | |
| 2017/0305968 A1 | 10/2017 | Tsein et al. | |
| 2018/0196058 A1 | 7/2018 | Kwong et al. | |
| 2018/0328941 A1 | 11/2018 | Bhatia et al. | |
| 2018/0335429 A1 | 11/2018 | Bhatia et al. | |
| 2019/0076081 A1* | 3/2019 | Hyde ................... | A61B 5/4238 |
| 2019/0128873 A1 | 5/2019 | Bhatia et al. | |
| 2019/0144917 A1 | 5/2019 | Bhatia et al. | |
| 2019/0212291 A1* | 7/2019 | Dudani ............ | G01N 33/54353 |
| 2019/0345534 A1* | 11/2019 | Kwong ................. | G01N 33/68 |
| 2019/0376113 A1* | 12/2019 | Bhatia ................... | C07K 11/02 |
| 2020/0096514 A1* | 3/2020 | Bhatia ...................... | C12Q 1/37 |
| 2020/0116725 A1 | 4/2020 | Bhatia et al. | |
| 2020/0225231 A1 | 7/2020 | Bhatia et al. | |
| 2020/0232986 A1 | 7/2020 | Bhatia et al. | |
| 2020/0249194 A9 | 8/2020 | Dudani et al. | |

FOREIGN PATENT DOCUMENTS

| | | |
|---|---|---|
| CN | 108484847 A | 9/2018 |
| JP | 2004-506900 A | 3/2004 |
| JP | 2004-129651 A | 4/2004 |
| JP | 2007-24631 A2 | 2/2007 |
| JP | 2007-206054 A | 8/2007 |
| JP | 2009-108037 A | 5/2009 |
| JP | 2009-524688 A | 7/2009 |
| JP | 2009-538430 A | 11/2009 |
| JP | 2013-060452 A | 4/2013 |
| WO | WO 2002/014867 A2 | 2/2002 |
| WO | WO 2006/034370 A2 | 3/2006 |
| WO | WO 2007/060921 A1 | 5/2007 |
| WO | WO 2008/072676 A1 | 6/2008 |
| WO | WO 2008/093513 A1 | 8/2008 |
| WO | WO 2008/127019 A1 | 10/2008 |
| WO | WO 2009/124265 A1 | 10/2009 |
| WO | WO 2010/101628 A2 | 9/2010 |
| WO | WO 2011/008996 A2 | 1/2011 |
| WO | WO 2012/085080 A1 | 6/2012 |
| WO | WO 2012/125808 A1 | 9/2012 |
| WO | WO 2013/019681 A2 | 2/2013 |
| WO | WO 2014/107599 A2 | 7/2014 |
| WO | WO 2014/120619 A2 | 8/2014 |
| WO | WO 2014/197816 A1 | 12/2014 |
| WO | WO 2014/197840 A1 | 12/2014 |
| WO | WO 2018/064383 A1 | 4/2018 |
| WO | WO 2018/187688 A1 | 10/2018 |
| WO | WO 2018/227132 A1 | 12/2018 |

OTHER PUBLICATIONS

Nizio et al. Journal of Breath Research, vol. 10, No. 2, Apr. 2016, pp. 1-21.*

Chan et al. Nature Nanotechnology, vol. 15, published Jul. 20, 2020, pp. 792-800.*

(56) References Cited

OTHER PUBLICATIONS

International Preliminary Report on Patentability for Application No. PCT/US2019/020741, dated Sep. 17, 2020.
[No Author Listed] Summary for peptidase S01.010: granzyme B. MEROPS. Retrieved from <https://www.ebi.ac.uk/merops/cgi-bin/pepsum?id=S01.010;type=P>. Apr. 26, 2019. 2 pages.
[No Author Listed] Summary for peptidase S01.135: granzyme A. MEROPS. Retrieved from <https://www.ebi.ac.uk/merops/cgi-bin/pepsum?id=S01.135;type=P>. Apr. 26, 2019. 2 pages.
[No Author Listed] Summary for peptidase S01.146: granzyme K. MEROPS. Retrieved from <https://www.ebi.ac.uk/merops/cgi-bin/pepsum?id=S01.146;type=P>. Apr. 26, 2019. 2 pages.
[No Author Listed], DQ™ Gelatin From Pig Skin, Fluorescein Conjugate—Special Packaging. ThermoFisher Scientific. ENZCHEK® Gelatinase/Collagenase Assay Kit Product Information Sheet. Accessed on Jul. 14, 2020. Retrieved from: <https://www.thermofisher.com/order/catalog/product/D12054#/D12054>. 4 pages.
Aalipour et al., Engineered immune cells as highly sensitive cancer diagnostics. Nat Biotechnol. 2019;37:531-9.
Abrahamson et al., Isolation of six cysteine proteinase inhibitors from human urine. Their physicochemical and enzyme kinetic properties and concentrations in biological fluids. J Biol Chem. Aug. 25, 1986;261(24):11282-9.
Abudayyeh, Nanoparticle-Chaperoned Urinary "Synthetic Biomarkers" for Profiling Proteases in Cancer. Thesis. Department of Mechanical Engineering. Jun. 2012.
Acharige et al., Breath-based diagnosis of fungal infections. J Breath Res. Feb. 6, 2018;12(2):027108. doi: 10.1088/1752-7163/aa98a1.
Amstad et al., Photo- and thermoresponsive polymersomes for triggered release. Angew Chem Int Ed. 2012;51:1-6.
Anderson et al., Mass spectrometric quantitation of peptides and proteins using Stable Isotope Standards and Capture by Anti-Peptide Antibodies (SISCAPA). J Proteome Res. Mar.-Apr. 2004;3(2):235-44.
Asai et al., A colorimetric assay for plasma antithrombin III using a new synthetic peptide substrate (PS-915). Clin Chim Acta. Dec. 29, 1984;144(2-3):163-71.
Bartlett, Diagnostic tests for agents of community-acquired pneumonia. Clin Infect Dis. May 2011. 52(Suppl 4):S296-304. doi: 10.1093/cid/cir045.
Baruch et al., Enzyme activity—it's all about image. Trends Cell Biol. Jan. 2004;14(1):29-35.
Bascom et al., Use of Enzyme Tests in Characterization and Identification of Aerobic and Facultatively Anaerobic Gram-Positive Cocci. Clin Microbiol Rev. Apr. 1998; 11(2): 318-340.
Beauchamp et al., Real-time breath gas analysis for pharmacokinetics: monitoring exhaled breath by on-line proton-transfer-reaction mass spectrometry after ingestion of eucalyptol-containing capsules. J Breath Res. Jun. 2010;4(2):026006. doi: 10.1088/1752-7155/4/2/026006. Epub Apr. 22, 2010.
Becker et al., Thrombin: Structure, Biochemistry, Measurement, and Status in Clinical Medicine. J Thromb Thrombolysis. Jul. 1998;5(3):215-229.
Berger, Helicobacter pylori breath tests. BMJ. 2002;324:1263.
Blum et al., Noninvasive optical imaging of cysteine protease activity using fluorescently quenched activity-based probes. Nat Chem Biol. Oct. 3, 2007;3(10):668-77. Epub Sep. 9, 2007.
Böhm et al., uPA/PAI-1 ratios distinguish benign prostatic hyperplasia and prostate cancer. J Cancer Res Clin Oncol. Jul. 2013;139(7):1221-8. doi: 10.1007/s00432-013-1428-y. Epub Apr. 18, 2013.
Bonomi et al., Detection of enzyme activity through catalytic signal amplification with functionalized gold nanoparticles. Angew Chem Int Ed. 2011;50:2307-12.
Bounameaux et al., Plasma measurement of D-dimer as diagnostic aid in suspected venous thromboembolism: an overview. Thromb Haemost. Jan. 1994;71(1):1-6.
Buss et al., Protease activity sensors noninvasively classify bacterial infections and antibiotic responses. EBioMedicine. Dec. 2018;38:248-56. doi:10.1016/j.ebiom.2018.11.031.
Caliendo et al., Better Tests, Better Care: Improved Diagnostics for Infectious Diseases. Clin Infect Dis. Dec. 2013;57(3):S139-S170.
Castillo et al., Sensitive substrates for human leukocyte and porcine pancreatic elastase: A study of the merits of various chromophoric and fluorogenic leaving groups in assays for serine proteases. Anal Biochem. Oct. 1979;99(1):53-64.
Chan et al., Inhalable Nanosensors for Rapid Breath-Based Pathogen Identification in Respiratory Infection. Revolutions in Biotechnology. MIT. Presented Mar. 5-6, 2018 at Tang Center, MIT Campus. 1 page.
Chen et al., A unique substrate recognition profile for matrix metalloproteinase-2. J Biol Chem. Feb. 8, 2002;277(6):4485-91.
Cheng et al., Multifunctional nanoparticles: Cost versus benefit of adding targeting and imaging capabilities. Sci. Nov. 16, 2012;338(6109):903-10.
Cheng et al., Ultrasensitive scanometric strategy for detection of matrix metalloproteinases using a histidine tagged peptide—Au nanoparticle probe. Chem Commun. 2011;47:2877-9.
Coelho et al., Usefulness of C-reactive protein in monitoring the severe community-acquired pneumonia clinical course. Crit Care. Aug. 2007; 11(4):R92.
Cohen et al., Detection and localization of surgically resectable cancers with a multi-analyte blood test. Science. 2018;3247(80):1-10.
Daniel et al., Implantable diagnostic device for cancer monitoring. Biosens Bioelectron. Jul. 15, 2009;24(11):3252-7. Epub Apr. 16, 2009.
De La Rica et al., Enzyme-responsive nanoparticles for drug release and diagnostics. Adv Drug Deliv Rev. Aug. 2012;64(11):967-78. doi: 10.1016/j.addr.2012.01.002. Epub Jan. 14, 2012.
Deng et al., Gold nanoparticles based molecular beacons for in vitro and in vivo detection of the matriptase expression on tumor. Biosens Bioelectron. Nov. 15, 2013;49:216-21. doi: 10.1016/j.bios.2013.05.018. Epub May 25, 2013.
Dennis et al., Albumin binding as a general strategy for improving the pharmacokinetics of proteins. J Biol Chem. Sep. 20, 2002;277(38):35035-43. Epub Jul. 15, 2002.
Deshpande et al., Current trends in the use of liposomes for tumor targeting. Nanomedicine (Lond). Sep. 2013;8(9):1509-28. doi:10.2217/nnm 13 118.
Dranoff, Cytokines in cancer pathogenesis and cancer therapy. Nat Rev Cancer. Jan. 2004;4(1):11-22.
D'Souza et al., A strategy for blood biomarker amplification and localization using ultrasound. Proc Natl Acad Sci U S A. Oct. 6, 2009;106(40):17152-7. doi: 10.1073/pnas.0903437106. Epub Sep. 23, 2009.
Dudani et al., Classification of prostate cancer using a protease activity nanosensor library. Proc Natl Acad Sci U S A Sep. 4, 2018;115(36):8954-8959. doi: 10.1073/pnas.1805337115. Epub Aug. 20, 2018.
Dudani et al., Harnessing Protease Activity to Improve Cancer Care. Ann Rev Cancer Biol. Mar. 2018;2:353-376.
Dudani et al., Photoactivated Spatiotemporally-Responsive Nanosensors of in Vivo Protease Activity. ACS Nano. Dec. 22, 2015;9(12):11708-17. doi: 10.1021/acsnano.5b05946. Epub Nov. 13, 2015.
Dudani et al., Sustained-release synthetic biomarkers for monitoring thrombosis and inflammation using point-of-care compatible readouts. Adv Funct Mater. May 3, 2016;26(17):2919-2928. doi: 10.1002/adfm.201505142. Epub Mar. 22, 2016.
El Badrawy et al., Matrix Metalloproteinase-9 Expression in Lung Cancer Patients and Its Relation to Serum MMP-9 Activity, Pathologic Type, and Prognosis. J Bronchol Interven Pulmonol. Oct. 2014; 21(4):327-34. doi: 10.1097/LBR.0000000000000094.
Elegbede et al., Mechanistic studies of the triggered release of liposomal contents by matrix metalloproteinase-9. J Am Chem Soc. Aug. 13, 2008;130(32):10633-42. doi: 10.1021/ja801548g. Epub Jul. 22, 2008.
Elston et al., New continuous and specific fluorometric assays for Pseudomonas aeruginosa elastase and LasA protease. Anal Biochem. Sep. 2007;368(1):87-94.
Farrell et al., Non-motor parkinsonian pathology in aging A53T ?-synuclein mice is associated with progressive synucleinopathy

(56) References Cited

OTHER PUBLICATIONS and altered enzymatic function. J Neurochem. Feb. 2014;128(4):536-46. doi: 10.1111/jnc.12481. Epub Nov. 20, 2013.
Fernandez et al., Volatile Biomarkers in Breath Associated With Liver Cirrhosis—Comparisons of Pre- and Post-liver Transplant Breath Samples. EBIOM. 2015;2:1243-50.
Figueiredo et al., Near infrared thoracoscopy of tumoral protease activity for improved detection of peripheral lung cancer. Int J Cancer. Jun. 2006;118(11):2672-7. doi: 10.1002/ijc.21713.
Fowlkes et al., Proteolysis of insulin-like growth factor binding protein-3 during rat pregnancy: a role for matrix metalloproteinases. Endocrinology. Dec. 1994;135(6):2810-3.
Fusaro et al., Prediction of high-responding peptides for targeted protein assays by mass spectrometry. Nat Biotechnol. Feb. 2009;27(2):190-8. doi: 10.1038/nbt.1524. Epub Jan. 25, 2009.
Gaieska et al., Impact of time to antibiotics on survival in patients with severe sepsis or septic shock in whom early goal-directed therapy was initiated in the emergency department. Crit Care Med. Apr. 2010;38(4):1045-53. doi: 10.1097/CCM.0b013e3181cc4824.
Galati et al., Increased resistance of peptides to serum proteases by modification of their amino groups. Resist peptides against serum proteases. Jan. 8, 2003;58:558-61.
Gartrell et al., Managing bone metastases and reducing skeletal related events in prostate cancer. Nat Rev Clin Oncol. Jun. 2014;11(6):335-45. doi: 10.1038/nrclinonc.2014.70. Epub May 13, 2014. Review. Erratum in: Nat Rev Clin Oncol. Jan. 2015;12(1). doi:10.1038/nrclinonc.2014.70.
Genbank Submission; NIH/NCBI, Accession No. 2WV1_A; Kovalevskiy et al.; Mar. 24, 2010.
Genbank Submission; NIH/NCBI, Accession No. CAG01641; Mar. 17, 2004.
Genbank Submission; NIH/NCBI, Accession No. NP_731669; Hoskins et al.; Dec. 18, 2009.
Genbank Submission; NIH/NCBI, Accession No. NP_938673; Cerdeno-Tarraga et al.; Jun. 3, 2010.
Genbank Submission; NIH/NCBI, Accession No. XP_001385378; Jeffries et al.; Apr. 11, 2008.
Genbank Submission; NIH/NCBI, Accession No. XP_002097000; Clark et al.; Aug. 12, 2009.
Genbank Submission; NIH/NCBI, Accession No. XP_00234527.; Jul. 7, 2006.
Genbank Submission; NIH/NCBI, Accession No. ZP_03507634; Gonzalez et al.; Dec. 19, 2008.
Genbank Submission; NIH/NCBI, Accession No. ZP_06431346; Small et al.; Jun. 9, 2010.
Ghadiali, James E. et al., "Enzyme-Responsive Nanoparticle Systems," Advanced Materials, vol. 20(22):4359-4363 (2008).
Ghoshal et al., How to Interpret Hydrogen Breath Tests. J Neurogastroenterol Motil. 2011;17:312-7.
Giljohann, et al., Drivers of biodiagnostic development. Nature. Nov. 26, 2009;462(7272):461-4. doi: 10.1038/nature08605.
Ginsberg et al., Sensitivity and specificity of a rapid whole-blood assay for D-dimer in the diagnosis of pulmonary embolism. Ann Intern Med. Dec. 15, 1998;129(12):1006-11.
Grayson et al., Multi-pulse drug delivery from a resorbable polymeric microchip device. Nat Mater. Nov. 2003;2(11):767-72.
Gross, Mass Spectrometry: A Textbook. Springer. 2nd ed. Mar. 1, 2011. Chapter 9. 415-452.
Guimaraes et al., Site-specific C-terminal internal loop labeling of proteins using sortase-mediated reactions. Nat Protoc. 2013;8:1787-99.
Haiko et al., The omptins of Yersinia pestis and *Salmonella enterica* cleave the reactive center loop of plasminogen activator inhibitor 1. J Bacteriol. Sep. 2010;192(18):4553-61. doi: 10.1128/JB.00458-10. Epub Jul. 16, 2010.
Haro et al., Matrix metalloproteinase-7-dependent release of tumor necrosis factor-alpha in a model of herniated disc resorption. J Clin Invest. Jan. 2000;105(2):143-50.

Harris et al., Protease-triggered unveiling of bioactive nanoparticles. Small. 2008;4(9):1307-12. doi: 10.1002/smll.200701319. Epub Aug. 8, 2008.
Haskins, The application of stable isotopes in biomedical research. Biomed Mass Spectrom. Jul. 1982;9(7):269-77.
Haun et al., Micro-NMR for rapid molecular analysis of human tumor samples. Sci Transl Med. Feb. 2011;3(71):71ra16. doi: 10.1126/scitranslmed.3002048.
Heaney et al., Real-time monitoring of exhaled volatiles using atmospheric pressure chemical ionization on a compact mass spectrometer. Bioanalysis. Jul. 2016;8(13):1325-36. doi: 10.4155/bio-2016-0045. Epub Jun. 9, 2016.
Herbig et al., Towards standardization in the analysis of breath gas volatiles. J Breath Res. 2014;8:1-11.
Holliday et al., Rapid Identification of *Staphylococcus aureus* by Using Fluorescent Staphylocoagulase Assays. J Clin Microbiol. Apr. 1999;37(4):1190-2.
Imai et al., Degradation of decorin by matrix metalloproteinases: identification of the cleavage sites, kinetic analyses and transforming growth factor-beta1 release. Biochem J. Mar. 15, 1997;322 (Pt 3):809-14.
Ito et al., Degradation of interleukin 1beta by matrix metalloproteinases. J Biol Chem. Jun. 21, 1996;271(25):14657-60.
Iwasaki et al., Control of adaptive immunity by the innate immune system. Nat Immunol. Mar. 19, 2015;16(4):343-53.
Jaffer et al., In vivo imaging of thrombin activity in experimental thrombi with thrombin-sensitive near-infrared molecular probe. Arterioscler Thromb Vasc Biol. Nov. 1, 2002;22(11):1929-35.
Janzen et al., Colorimetric sensor arrays for volatile organic compounds. Anal Chem. Jun. 1, 2006;78(11):3591-600.
Jiang et al., Tumor imaging by means of proteolytic activation of cell-penetrating peptides. Proc. Natl. Acad. Sci. U. S. A. 2004;101:17867-17872.
Johnson et al., Active-site gating regulates substrate selectivity in a chymotrypsin-like serine protease the structure of haemophilus influenzae immunoglobulin A1 protease. J Mol Biol. Jun. 12, 2009;389(3):559-74. doi: 10.1016/j.jmb.2009.04.041. Epub Apr. 23, 2009.
Johnson et al., Computer program (SEQPEP) to aid in the interpretation of high-energy collision tandem mass spectra of peptides. Biomed Environ Mass Spectrom. Nov. 1989;18(11):945-57.
Kalinska et al., Substrate specificity of *Staphylococcus aureus* cysteine proteases—Staphopains A, B and C. Biochimie. Feb. 2012;94(2):318-27. doi: 10.1016/j.biochi.2011.07.020. Epub Jul. 23, 2011.
Kaman et al., Evaluation of a FRET-Peptide Substrate to Predict Virulence in Pseudomonas aeruginosa. PLoS One; Nov. 2013;8(11):e81428.
Kaminskas et al., Methotrexate-conjugated PEGylated dendrimers show differential patterns of deposition and activity in tumor-burdened lymph nodes after intravenous and subcutaneous administration in rats. Mol Pharm. Feb. 2, 2015;12(2):432-43. doi: 10.1021/mp500531e. Epub Jan. 20, 2015.
Kasperkiewicz et al., Design of ultrasensitive probes for human neutrophil elastase through hybrid combinatorial substrate library profiling. PNAS. 2014;111:2518-23.
Kastelic et al., Stefin B, the major low molecular weight inhibitor in ovarian carcinoma. Cancer Lett. Jul. 15, 1994;82(1):81-8.
Kim et al., Applications of stable, nonradioactive isotope tracers in in vivo human metabolic research. Exp Mol Med. Jan. 2016; 48(1): e203. Epub Jan. 15, 2016. doi: 10.1038/emm.2015.97.
Kircher et al., A dual fluorochrome probe for imaging proteases. Bioconjug Chem. Mar.-Apr. 2004;15(2):242-8.
Kirkpatrick et al., Noninvasive lung cancer detection via pulmonary protease profiling. bioRxiv. 36 pages. doi: https://doi.org/10.1101/495259.
Klotz et al., Management of low risk prostate cancer-active surveillance and focal therapy. Nat Rev Clin Oncol. Jun. 2014;11(6):324-34. doi: 10.1038/nrclinonc.2014.73. Epub May 13, 2014.
Krebs et al., Molecular analysis of circulating tumour cells-biology and biomarkers. Nat Rev Clin Oncol. 2014;11:129-44.
Krilaviciute et al., Detection of cancer through exhaled breath?: a systematic review Literature search. Oncotarget. 2015;6:38643-57.

(56) References Cited

OTHER PUBLICATIONS

Ku et al., In vivo sensing of proteolytic activity with an NSET-based NIR fluorogenic nanosensor. Biosens Bioelectron. Mar. 15, 2016;77:471-7. doi: 10.1016/j.bios.2015.09.067. Epub Sep. 30, 2015.

Kuhn et al., Developing multiplexed assays for troponin I and interleukin-33 in plasma by peptide immunoaffinity enrichment and targeted mass spectrometry. Clin Chem. Jun. 2009;55(6):1108-17. doi: 10.1373/clinchem.2009.123935. Epub Apr. 16, 2009.

Kulkarni et al., MMP-9 Responsive PEG Cleavable Nanovesicles for Efficient Delivery of Chemotherapeutics to Pancreatic Cancer. Mol Pharm. Jul. 7, 2014; 11(7): 2390-2399. doi: 10.1021/mp500108p.

Kwak et al., Volatile disease biomarkers in breath: a critique. Curr Pharm Biotechnol; 2011;12:1067-74.

Kwon et al., Porous Silicon Nanoparticle Delivery of Tandem Peptide Anti?Infectives for the Treatment of Pseudomonas aeruginosa Lung Infections. Adv Mat. Sep. 20, 2017;29(35). 21pages.

Kwon et al., Ultrasensitive tumour-penetrating nanosensors of protease activity. Nat Biomed Eng. 2017;1. pii: 0054. doi:10.1038/s41551-017-0054. Epub Apr. 10, 2017.

Kwong et al., Mass-encoded synthetic biomarkers for multiplexed urinary monitoring of disease. Nat Biotechnol. Jan. 2013;31(1):63-70. doi: 10.1038/nbt.2464. Epub Dec. 16, 2012.

Kwong et al., Mathematical framework for activity-based cancer biomarkers. Proc Natl Acad Sci U S A. Oct. 13, 2015;112(41):12627-32. doi: 10.1073/pnas.1506925112. Epub Sep. 28, 2015.

Lange et al., Selected reaction monitoring for quantitative proteomics: a tutorial. Mol Syst Biol. 2008;4:222. doi: 10.1038/msb.2008.61. Epub Oct. 14, 2008.

Larsen et al., Assay of plasma heparin using thrombin and the chromogenic substrate H-D-Phe-Pip-Arg-pNA (S-2238). Thromb Res. Aug. 1978;13(2):285-8.

Laupland et al., The changing culture of the microbiology laboratory. Can J Infect Dis Med Microbiol. 2013 Autumn; 24(3):125-128. doi: 10.1155/2013/101630.

Lebeau et al., Imaging active urokinase plasminogen activator in prostate cancer. Cancer Res. Apr. 1, 2015;75(7):1225-35. doi:10.1158/0008-5472.CAN-14/2185. Epub Feb. 11, 2015.

Levi et al., Matrix metalloproteinase 2 releases active soluble ectodomain of fibroblast growth factor receptor 1. Proc Natl Acad Sci U S A. Jul. 9, 1996;93(14):7069-74.

Lin et al., Drug-induced amplification of nanoparticle targeting to tumors. Nano Today. Oct. 2014;9(5):550-559. doi:10.1016/j.nantod.2014.09.001. Epub Sep. 23, 2014.

Lin et al., Nanoparticles that sense thrombin activity as synthetic urinary biomarkers of thrombosis. ACS Nano. Oct. 22, 2013;7(10):9001-9. doi: 10.1021/nn403550c. Epub Sep. 12, 2013.

Liou et al., Nonisotropic Enzyme-Inhibitor Interactions: A Novel Nonoxidative Mechanism for Quantum Proteolysis by Human Neutrophils. Biochem. 1995;34(49):16171-7.

Liu et al., Structure-based programming of lymph-node targeting in molecular vaccines. Nature. Mar. 27, 2014;507(7493):519-22. doi: 10.1038/nature12978. Epub Feb. 16, 2014.

Loynachan et al., ANYL 234: Catalytic nanomaterials for amplified biosensing. Abstract of Papers, 256th National Meeting & Exposition of the ACS. ACS National Meeting & Exposition. Aug. 19, 2018. 1 page.

Mallick et al., Computational prediction of proteotypic peptides for quantitative proteomics. Nat Biotechnol. Jan. 2007;25(1):125-31. Epub Dec. 31, 2006.

Mañes et al., The matrix metalloproteinase-9 regulates the insulin-like growth factor-triggered autocrine response in DU-145 carcinoma cells. J Biol Chem. Mar. 12, 1999;274(11):6935-45.

Martinez et al., Diagnostics for the developing world: microfluidic paper-based analytical devices. Anal Chem. Jan. 1, 2010;82(1):3-10. doi: 10.1021/ac9013989.

Matsumoto et al., Role of bacterial proteases in pseudomonal and serratial keratitis. Biol Chem. Jan. 2004;385(11):1007-16.

McCarter et al., Substrate Specificity of the *Escherichia coli* Outer Membrane Protease OmpT. J Bacteriol. Sep. 2004; 186(17): 5919-5925. doi: 10.1128/JB.186.17.5919-5925.2004.

McLennan et al., Subcutaneous drug delivery and the role of the lymphatics. Drug Discov Today Technol. 2005 Spring;2(1):89-96. doi:10.1016/j.ddtec.2005.05.006.

Meyer et al., Respiratory protease / antiprotease balance determines susceptibility to viral infection and can be modified by nutritional antioxidants. Am J Physiol Lung Cell Mol Physiol. 2015;308:L1189-L1201.

Mira et al., Insulin-like growth factor I-triggered cell migration and invasion are mediated by matrix metalloproteinase-9. Endocrinology. Apr. 1999;140(4):1657-64.

Miritti et al., Expression of cystatins, high molecular weight cytokeratin, and proliferation markers in prostatic adenocarcinoma and hyperplasia. Prostate. Mar. 1, 2003;54(4):290-8.

Mitchell et al., Assay for plasma heparin using a synthetic peptide substrate for thrombin: introduction of the fluorophore aminoisophthalic acid, dimethyl ester. Thromb Res. Jul. 1978;13(1):47-52.

Morgia et al., Matrix metalloproteinases as diagnostic (MMP-13) and prognostic (MMP-2, MMP-9) markers of prostate cancer. Urol Res. Feb. 2005;33(1):44-50. Epub Oct. 22, 2004.

Morihara, Pseudolysin and other pathogen endopeptidases of thermolysin family. Methods in Enzymol. 1995;248:242-53.

Morris et al., Urine and plasma levels of fibrinopeptide B in patients with deep vein thrombosis and pulmonary embolism. Thromb Res. May 1, 2003;110(2-3):159-65.

Murray, What Is New in Clinical Microbiology—Microbial Identification by MALDI-TOF Mass Spectrometry. JMDI. 2012;14:419-23.

Nagase et al., Matrix metalloproteinases. J Biol Chem. Jul. 30, 1999;274(31):21491-4.

Nahrendorf et al., Hybrid in vivo FMT-CT imaging of protease activity in atherosclerosis with customized nanosensors. Arterioscler Thromb Vasc Biol. Oct. 2009;29(10):1444-51. doi:10.1161/ATVBAHA.109.193086. Epub Jul. 16, 2009. Supplemental Material.

Nomura et al., Activity-based protein profiling for biochemical pathway discovery in cancer. Nat Rev Cancer. Sep. 2010;10(9):630-8. doi: 10.1038/nrc2901. Epub Aug. 12, 2010.

Nouh et al., Cathepsin B: a potential prognostic marker for inflammatory breast cancer. J Transl Med. 2011;9(1):8 pages.

Olson et al., In vivo characterization of activatable cell penetrating peptides for targeting protease activity in cancer. Integr Biol (Camb). Jun. 2009; 1(5-6):382-93.

Olson et al., In vivo fluorescence imaging of atherosclerotic plaques with activatable cell-penetrating peptides targeting thrombin activity. Integr Biol (Camb). Jun. 2012;4(6):595-605. doi: 10.1039/c2ib00161f. Epub Apr. 26, 2012.

Ong et al., Use of Mass Spectrometric Vapor Analysis to Improve Canine Explosive Detection Efficiency. Anal Chem. 2017;89:6482-90.

Park et al., Magnetic Iron Oxide Nanoworms for Tumor Targeting and Imaging. Adv Mater. May 5, 2008;20(9):1630-1635.

Park et al., Systematic surface engineering of magnetic nanoworms for in vivo tumor targeting. Small. Mar. 2009;5(6):694-700. doi: 10.1002/sml1.200801789.

Parks et al., Matrix metalloproteinases as modulators of inflammation and innate immunity. Nat Rev Immunol. Aug. 2004;4(8):617-29.

Patton et al., Inhaling medicines: delivering drugs to the body through the lungs. Nat Rev Drug Discov. Jan. 2007;6(1):67-74.

Patton et al., The lungs as a portal of entry for systemic drug delivery. Proc Am Thorac Soc. 2004;1(4):338-44.

Peer et al., Nanocarriers as an emerging platform for cancer therapy. Nat Nanotechnol. Dec. 2007;2(12):751-60.

Phillips et al., Variation in volatile organic compounds in the breath of normal humans. J Chromatogr B. 1999;729:75-88.

Pomerantz et al., Determination of oligonucleotide composition from mass spectrometrically measured molecular weight. J Am Soc Mass Spectrom. Mar. 1993;4(3):204-9. doi: 10.1016/1044-0305(93)85082-9.

(56) References Cited

OTHER PUBLICATIONS

Posthuma-Trumpie et al., Lateral flow (immuno)assay: its strengths, weaknesses, opportunities and threats. A literature survey. Anal Bioanal Chem. Jan. 2009;393(2):569-82. doi: 10.1007/s00216-008-2287-2. Epub Aug. 13, 2008.
Potempa et al., Corruption of innate immunity by bacterial proteases. J Innate Immun. 2009;1(2):70-87.
Powell et al., The metalloproteinase matrilysin proteolytically generates active soluble Fas ligand and potentiates epithelial cell apoptosis. Curr Biol. Dec. 16-30, 1999;9(24):1441-7.
Prensner et al., Beyond PSA: the next generation of prostate cancer biomarkers. Sci Transl Med. Mar. 28, 2012;4(127):127rv3. doi:10.1126/scitranslmed.3003180.
Rajah et al., Elevated levels of the IGF-binding protein protease MMP-1 in asthmatic airway smooth muscle. Am J Respir Cell Mol Biol. Feb. 1999;20(2):199-208.
Rawlings et al., The MEROPS database of proteolytic enzymes, their substrates and inhibitors in 2017 and a comparison with peptidases in the PANTHER database. Nucleic Acid Res. Jan. 4, 2018;46(D1):D624-D632.
Rennke, How does glomerular epithelial cell injury contribute to progressive glomerular damage? Kidney Int Suppl. Feb. 1994;45:S58-63.
Rijkers et al., Design and synthesis of thrombin substrates with modified kinetic parameters. Thromb Res. Sep. 15, 1995;79(5-6):491-9.
Roepstorff et al., Proposal for a common nomenclature for sequence ions in mass spectra of peptides. Biomed Mass Spectrom. Nov. 1984;11(11):601.
Ross et al., Multiplexed protein quantitation in *Saccharomyces cerevisiae* using amine-reactive isobaric tagging reagents. Mol Cell Proteomics. Dec. 2004;3(12):1154-69. Epub Sep. 22, 2004.
Ross et al., Volatile compounds in blood headspace and nasal breath. J Breath Res. Sep. 13, 2017;11(4):046001. doi: 10.1088/1752-7163/aa7d10.
Rousalova et al., Granzyme B-induced apoptosis in cancer cells and its regulation (review). Int J Oncol. Dec. 2010;37(6):1361-78. doi: 10.3892/ijo_00000788. PMID: 21042704.
Roy et al., Matrix metalloproteinases as novel biomarkers and potential therapeutic targets in human cancer. J Clin Oncol. 2009;27:5287-97.
Ruoslahti et al., Targeting of drugs and nanoparticles to tumors. J Cell Biol. Mar. 22, 2010;188(6):759-68. doi: 10.1083/jcb.200910104. Epub Mar. 15, 2010.
Santini et al., A controlled-release microchip. Nature. Jan. 28, 1999;397(6717):335-8.
Sawyers, The cancer biomarker problem. Nature. Apr. 3, 2008;452(7187):548-52. doi: 10.1038/nature06913.
Schmid et al., Albumin-binding prodrugs of camptothecin and doxorubicin with an ala-leu-ala-leu-linker that are cleaved by cathepsin b: synthesis and antitumor efficacy. Bioconj Chem. 2007;18(3):702-16.
Schonbeck et al., Generation of biologically active IL-1 beta by matrix metalloproteinases: a novel caspase-1-independent pathway of IL-1 beta processing. J Immunol. Oct. 1, 1998;161(7):3340-6.
Schuerle et al., Magnetically Actuated Protease Sensors for in Vivo Tumor Profiling. Nano Lett. Oct. 12, 2016;16(10):6303-6310. Epub Sep. 13, 2016.
Sethi et al., Clinical application of volatile organic compound analysis for detecting infectious diseases. Clin Microbiol Rev. Jul. 2013;26(3):462-75. doi: 10.1128/CMR.00020-13.
Shariat et al., Urine detection of survivin is a sensitive marker for the noninvasive diagnosis of bladder cancer. J Urol. Feb. 2004;171(2 Pt 1):626-30.
Shaw et al., The role and regulation of the extracellular proteases of *Staphylococcus aureus*. Microbiol. Jan. 2004;150:217-28. doi: 10.1099/mic.0.26634-0.
Shibuya et al., Pseudomonas aeruginosa alkaline proteinase might share a biological function with plasmin. Biochim Biophys Acta. Apr. 29, 1991; 1077(3):316-24.

Smith et al., Rapid identification of highly active and selective substrates for stromelysin and matrilysin using bacteriophage peptide display libraries. J Biol Chem. Mar. 24, 1995;270(12):6440-9.
Stach et al., Unique Substrate Specificity of SplE Serine Protease from *Staphylococcus aureus*. Structure. Apr. 3, 2018;26(4):572-579.e4. doi: 10.1016/j.str.2018.02.008. Epub Mar. 8, 2018.
Stein et al., Ultrasensitive Scaffold-Dependent Protease Sensors with Large Dynamic Range. ACS Synth Biol. Jul. 21, 2017;6(7):1337-1342. doi: 10.1021/acssynbio.6b00370. Epub Mar. 28, 2017.
Sugahara et al., Coadministration of a tumor-penetrating peptide enhances the efficacy of cancer drugs. Science. May 21, 2010;328(5981):1031-5. doi:10.1126/science.1183057. Epub Apr. 8, 2010.
Sutherland et al., RGD-Binding Integrins in Prostate Cancer: Expression Patterns and Therapeutic Prospects against Bone Metastasis. Cancers (Basel). Oct. 26, 2012;4(4):1106-45. doi:10.3390/cancers4041106.
Suzuki et al., Matrix metalloproteinase-3 releases active heparin-binding EGF-like growth factor by cleavage at a specific juxtamembrane site. J Biol Chem. Dec. 12, 1997;272(50):31730-7.
Sweeney et al., Robust classification of bacterial and viral infections via integrated host gene expression diagnostics. Sci Transl Med. Jul. 2016;8(346):346ra91.
Tascilar et al., Role of tumor markers and mutations in cells and pancreatic juice in the diagnosis of pancreatic cancer. Ann Oncol. 1999;10 Suppl 4:107-10.
Taylor et al., Integrative genomic profiling of human prostate cancer. Cancer Cell. Jul. 13, 2010;18(1):11-22. doi:10.1016/j.ccr.2010.05.026. Epub Jun. 24, 2010.
Thomassin et al., OmpT Outer Membrane Proteases of Enterohemorrhagic and Enteropathogenic *Escherichia coli* Contribute Differently to the Degradation of Human LL-37. Infect Immun. Feb. 2012; 80(2): 483-492. doi: 10.1128/IAI.05674-11.
Thompson et al., Tandem mass tags: a novel quantification strategy for comparative analysis of complex protein mixtures by MS/MS. Anal Chem. Apr. 15, 2003;75(8):1895-904. Erratum in: Anal Chem. Sep. 15, 2003;75(18):4942. Johnstone, R [added]. Anal Chem. Jun. 15, 2006;78(12):4235. Mohammed, A Karim A [added].
Thorek et al., Internalization of secreted antigen-targeted antibodies by the neonatal Fc receptor for precision imaging of the androgen receptor axis. Sci Transl Med. Nov. 30, 2016;8(367):367ra167.
Tockman et al., Considerations in bringing a cancer biomarker to clinical application. Cancer Res. May 1, 1992;52(9 Suppl):2711s-2718s.
Trapani et al., Killing by cytotoxic T cells and natural killer cells: multiple granule serine proteases as initiators of DNA fragmentation. Immunol Cell Biol. 1993;71(3):201-8.
Traxlmayr et al., Strong Enrichment of Aromatic Residues in Binding Sites from a Charge-neutralized Hyperthermostable Sso7d Scaffold Library. J Biol Chem. Oct. 21, 2016;291(43):22496-22508. Epub Aug. 30, 2016.
Truong et al., Isotope-coded chemical reporter and acid-cleavable affinity reagents for monitoring protein sulfenic acids. Bioorg Med Chem Lett. Sep. 1, 2011;21(17):5015-20. doi: 10.1016/j.bmcl.2011.04.115. Epub May 3, 2011.
Tung et al., A novel near-infrared fluorescence sensor for detection of thrombin activation in blood. Chembiochem. Mar. 1, 2002;3(2-3):207-11.
Van Der Schee et al., Breathomics in lung disease. Chest. 2015;147:224-31.
Vandooren et al., Zymography Methods for Visualizing Hydrolytic Enzymes. Nat Methods. Mar. 2013;10(3):211-20. doi: 10.1038/nmeth.2371.
Vasiljeva et al., Monitoring protease activity in biological tissues using antibody prodrugs as sensing probes. Sci Rep. Apr. 3, 2020;10(1):5894.
Vessillier et al., Hydrolysis of glycine-containing elastin pentapeptides by LasA, a metalloelastase from Pseudomonas aeruginosa. Eur J Biochem. Feb. 2001;268(4):1049-57.
Wang et al., Intrinsic enzyme mimicking activity of gold nanoclusters upon visible light triggering and its application for colorimetric trypsin detection. Biosens Bioelectronics. 2015;64:523-9. Epub Sep. 30, 2014.

(56) References Cited

OTHER PUBLICATIONS

Warren et al., Disease detection by ultrasensitive quantification of microdosed synthetic urinary biomarkers. J Am Chem Soc. 2014;136:13709-14.
Warren et al., Harnessing protease activity to improve cancer care. Annual Rev Cancer Biol. 2018;2:353-76.
Warren et al., Point-of-care diagnostics for noncommunicable diseases using synthetic urinary biomarkers and paper microfluidics. Proc Natl Acad Sci U S A. Mar. 11, 2014;111(10):3671-6. doi:10.1073/pnas.1314651111. Epub Feb. 24, 2014.
Weissleder et al., In vivo imaging of tumors with protease-activated near-infrared fluorescent probes. Nat Biotechnol. Apr. 1999;17(4):375-8.
Welser et al., Protease responsive nanoprobes with tethered fluorogenic peptidyl 3-arylcoumarin substrates. Chem Commun (Camb). Feb. 14, 2009;(6):671-3. Epub Dec. 8, 2008.
Welser et al., Protease sensing with nanoparticle based platforms. Analyst. Jan. 7, 2011;136(1):29-41. doi: 10.1039/c0an00429d. Epub Sep. 28, 2010.
Whiteaker et al., An automated and multiplexed method for high throughput peptide immunoaffinity enrichment and multiple reaction monitoring mass spectrometry-based quantification of protein biomarkers. Mol Cell Proteomics. Jan. 2010;9(1):184-96. doi: 10.1074/mcp.M900254-MCP200. Epub Oct. 20, 2009.
Whiteaker et al., Antibody-based enrichment of peptides on magnetic beads for masss spectrometry-based quantification of serum biomarkers. Anal Biochem. Mar. 1, 2007;362(1):44-54. Epub Dec. 20, 2006.
Whitney et al., Ratiometric activatable cell-penetrating peptides provide rapid in vivo readout of thrombin activation. Angew Chem Int Ed Engl. Jan. 2, 2013;52(1):325-30. doi: 10.1002/anie.201205721. Epub Oct. 18, 2012.
Wildeboer et al., Characterization of bacterial proteases with a panel of fluorescent peptide substrates. Anal Biochem. Jan. 15, 2009;384(2):321-8. doi: 10.1016/j.ab.2008.10.004. Epub Oct. 11, 2008.
Wilkinson et al., Ventilator-Associated Pneumonia Is Characterized by Excessive Release of Neutrophil Proteases in the Lung. Chest. Dec. 2012;142(6):1425-32.
Wilson et al., Applications and Advances in Electronic-Nose Technologies. Sensors (Basel). 2009;9(7):5099-148. doi: 10.3390/s90705099. Epub Jun. 29, 2009.
Withana et al., Labeling of active proteases in fresh-frozen tissues by topical application of quenched activity-based probes. Nat Protoc. Jan. 2016;11(1):184-91. doi: 10.1038/nprot.2016.004. Epub Dec. 30, 2015.
Wollscheid et al., Mass-spectrometric identification and relative quantification of N-linked cell surface glycoproteins. Nat Biotechnol. Apr. 2009;27(4):378-86. doi: 10.1038/nbt.1532. Epub Apr. 6, 2009. Erratum in: Nat Biotechnol. Sep. 2009;27(9):864.
Wu et al., Expression and clinical significance of matrix metalloproteinase-9 in lymphatic invasiveness and metastasis of breast cancer. PLOS ONE. 2014;9(5):e97804.
Xia et al., Multiplex detection of protease activity with quantum dot nanosenors prepared by Intein-Mediated specific bioconjugation. Analytical Chemistry. Nov. 15, 2008; 22(80) 8649-8655.

Yager et al., Point-of-care diagnostics for global health. Annu Rev Biomed Eng. 2008;10:10744. doi: 10.1146/annurev.bioeng.10.061807.160524.
Yan et al., In Situ Zymography: A Molecular Pathology Technique to Localize Endogenous Protease Activity in Tissue Sections. Vet Pathol May 2003;40(3):227-36.
Yu et al., Cell surface-localized matrix metalloproteinase-9 proteolytically activates TGF-beta and promotes tumor invasion and angiogenesis. Genes Dev. Jan. 15, 2000;14(2):163-76.
Zhang et al., Identification and quantification of N-linked glycoproteins using hydrazide chemistry, stable isotope labeling and mass spectrometry. Nat Biotechnol. Jun. 2003;21(6):660-6. Epub May 18, 2003.
Zheng et al., Dual-reaction triggered sensitivity amplification for ultrasensitive peptide-cleavage based electrochemical detection of matrix metalloproteinase-7. Biosens Bioelectronics. 2018;103:46-52. Epub Feb. 21, 2018.
Zhou et al., Thermo-sensitive microgels supported gold nanoparticles as temperature-mediated catalyst. Chinese J Polym Sci. 2019;37:235-42. Epub Aug. 30, 2018.
Zieske, A perspective on the use of iTRAQ reagent technology for protein complex and profiling studies. J Exp Bot. 2006;57(7):1501-8. Epub Mar. 30, 2006.
Zumla et al., Rapid point of care diagnostic tests for viral and bacterial respiratory tract infections-needs, advances, and future prospects. Lancet Infect Dis. 2014;14(11):1123-35.
International Search Report and Written Opinion dated May 21, 2019 for Application No. PCT/US2019/020741.
Adiguzel et al., Breath sensors for lung cancer diagnosis. Biosens Bioelectron. Mar. 15, 2015;65:121-38. doi: 10.1016/j.bios.2014.10.023. Epub Oct. 19, 2014.
Figueiredo et al., Folic acid and prevention of colorectal adenomas: a combined analysis of randomized clinical trials. Int J Cancer. Jul. 1, 2011;129(1):192-203. doi: 10.1002/ijc.25872. Epub Apr. 1, 2011.
Grimm et al., Use of Gene Expression Profiling to Direct in Vivo Molecular Imaging of Lung Cancer. PNAS. Oct. 4, 2005;102(40):14404-9.
Nizio et al., In vitro volatile organic compound profiling using GCxGC-TOFMS to differentiate bacteria associated with lung infections: a proof-of-concept study. J Breath Res. Apr. 27, 2016;10:026008, 12 pages.
Ong et al., Inhalable nanosensors for rapid breath-based pathogen identification in respiratory infection. Adv Res Technol Symp. Mar. 5, 2018. 2 pages
Peng et al., Diagnosing lung cancer in exhaled breath using gold nanoparticles. Nat Nanotechnol. Oct. 2009;4(10):669-73. doi: 10.1038/nnano.2009.235. Epub Aug. 30, 2009.
Salaun et al., MMP-13 In-Vivo Molecular Imaging Reveals Early Expression in Lung Adenocarcinoma. Plos One. 2015;10(7):e0132960, 19 pages. Epub Jul. 20, 2015. doi: 10.1371/journal.pone.0132960.
Schulenburg et al., A FRET-based biosensor for the detection of neutrophil elastase. Analyst. Mar. 7, 2016;141(5):1645-8. doi: 10.1039/c5an01747e.
Zhu et al., Detecting bacterial lung infections: in vivo evaluation of in vitro volatile fingerprints. J Breath Res. Jan. 10, 2013;7(1):016003, 7 pages.

\* cited by examiner

| | $k_{cat}$, s$^{-1}$ | $K_m$, μM | $k_{cat}/K_m$, M$^{-1}$·s$^{-1}$ |
| --- | --- | --- | --- |
| NE sensor_PFP | 2.60 | 25.7 | 1.01 × 10$^5$ |
| NE sensor_HFB | 0.218 | 1.53 | 1.43 × 10$^5$ |

| t = 0 h | t = 24 h | t = 26 h |
| --- | --- | --- |
| Infect CD-1 mice with 1.5 × 10$^8$ cfu PAO1/mouse | Euthanize mice Prepare lung homogenate | Mix homogenates with nanosensors and measure reporter in headspace over time |

| VOC | MW | VP (mm Hg at 25°C) | BP (°C at 760 mm Hg) |
|---|---|---|---|
| Methanethiol | 48.108 | 1510 | 43 |
| 2-Propene-1-thiol | 74.141 | 524 | 67 |
| 2-Propanethiol | 76.16 | 277.3 | 57 |
| 1-Propanethiol | 76.16 | 154 | 68 |
| 2-Methyl-1-propanethiol | 90.19 | 74.12 | 87 |
| 1-Butanethiol | 90.19 | 45.5 | 98 |
| 2-Pentanethiol | 104.21 | 23.2 | 112 |
| 3-Methyl-1-butanethiol | 104.21 | 23.2 | 119 |
| 1-Pentanethiol | 104.21 | 13.8 | 126 |
| Ethanol | 46.069 | 59.3 | 78.2 |
| Propanol | 60.1 | 21 | 97.2 |
| Isopropyl alcohol | 60.1 | 45.4 | 82 |
| Isobutyl alcohol | 74.123 | 10.4 | 108 |
| Butyl alcohol | 74.123 | 7 | 117 |
| 2-Methyl-3-buten-2-ol | 86.13 | 23.5 | 98 |
| 1-Penten-3-ol | 86.13 | 11.2 | 114 |
| Isoamyl alcohol | 88.15 | 2.37 | 132 |
| Amyl alcohol | 88.15 | 2.2 | 138 |

FIG. 13

| Pathogen | Protease | Class | Natural/synthetic substrate | Ref. |
|---|---|---|---|---|
| P. aeruginosa | Elastase B | metallo | Plasminogen activator inhibitor 1<br>Z-AG+LA | 46, 47 |
| | Elastase A | metallo | LGG+GA | 48 |
| | Alkaline protease | metallo | VLK-AMC | 49 |
| | lmelysin | metallo | LGR-AMC | 50 |
| | Protease IV | serine | GPK-AMC | 50 |
| S. aureus | Aureolysin | metallo | Plasminogen activator inhibitor 1 | 51 |
| | Coagulase* | NA* | VPR-AMC | 52 |
| | V8 | serine | Z-FLE-AMC<br>Z-LLE-AMC | 53 |
| | SplE | serine | YLH-AMC | 54 |
| | Staphopain A | cysteine | FGAK-AMC | 55 |
| | Staphopain B | cysteine | IAAG-AMC | 55 |
| | Staphopain C | cysteine | IAKD-AMC | 55 |
| K. pneumoniae | Kop peptidase | aspartic | Plasminogen activator inhibitor 1 | 46 |
| E. coli | OmpT | serine | cleaves at dibasic sites | 56, 57 |
| S. pneumoniae and H. influenzae | IgA1 protease | metallo | cleaves proline hinge region (P235-T236) of IgA** | 58 |
| Other bacteria | Subtilisin (B.licheniformens) | serine | Suc-AAF-AMC<br>Z-GGL-AMC<br>Boc-QAR-AMC<br>Suc-LLVY-AMC<br>Z-GAH-AMC | 53 |
| | Protease XIV (S.griseus) | serine | PFR-AMC<br>Z-RR-AMC<br>Z-FR-AMC<br>Z-GGR-AMC<br>Boc-GKR-AMC<br>Suc-AFK-AMC | |

+ indicates cleavage site for substrates where P1 site is not last residue
*binds prothrombin (serine protease) to generate active protease activity
**IgA not present in mice

FIG. 14

SEQUENCE LISTING

<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 1

Leu Gly Gly Gly Ala
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 2

Lys Ile Thr Ala Gln Asp Asp Glu Glu Ser
1               5                   10

<210> SEQ ID NO 3
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 3

Ala Ala Phe Ala
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (4)..(4)
<223> OTHER INFORMATION: modified by PEG4

<400> SEQUENCE: 4

Cys Lys Lys Lys
1

<210> SEQ ID NO 5
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: modified by a Z protecting group

<400> SEQUENCE: 5

Ala Gly Leu Ala
1

<210> SEQ ID NO 6
<211> LENGTH: 4
<212> TYPE: PRT

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (4)..(4)
<223> OTHER INFORMATION: modified by 7-amino-4-methylcoumarin

<400> SEQUENCE: 6

Phe Gly Ala Lys
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (4)..(4)
<223> OTHER INFORMATION: modified by 7-amino-4-methylcoumarin

<400> SEQUENCE: 7

Ile Ala Ala Gly
1

<210> SEQ ID NO 8
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (4)..(4)
<223> OTHER INFORMATION: modified by 7-amino-4-methylcoumarin

<400> SEQUENCE: 8

Ile Ala Lys Asp
1

<210> SEQ ID NO 9
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: modified by Suc protecting group
<220> FEATURE:
<221> NAME/KEY: MISC_FEATURE
<222> LOCATION: (4)..(4)
<223> OTHER INFORMATION: modified by 7-amino-4-methylcoumarin

<400> SEQUENCE: 9

Leu Leu Val Tyr
1

<210> SEQ ID NO 10
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: 6-benzyloxynorleucine
```

```
<220> FEATURE:
<221> NAME/KEY: MISC_FEATURE
<222> LOCATION: (2)..(2)
<223> OTHER INFORMATION: methionine dioxide
<220> FEATURE:
<221> NAME/KEY: MISC_FEATURE
<222> LOCATION: (3)..(3)
<223> OTHER INFORMATION: Octahydroindolecarboxylic acid
<220> FEATURE:
<221> NAME/KEY: MISC_FEATURE
<222> LOCATION: (4)..(4)
<223> OTHER INFORMATION: alpha-Aminobutyric acid

<400> SEQUENCE: 10

Xaa Xaa Xaa Xaa
1
```

INHALABLE NANOSENSORS WITH VOLATILE REPORTERS AND USES THEREOF

RELATED APPLICATIONS

This application claims the benefit under 35 U.S.C. § 119(e) of U.S. Provisional Application No. 62/638,352, entitled "INHALABLE NANOSENSORS WITH VOLATILE REPORTERS AND USES THEREOF," filed Mar. 5, 2018, the contents of which is incorporated herein by reference in its entirety.

GOVERNMENT SUPPORT

This invention was made with Government support under Grant No. FA8702-15-D-0001 awarded by the U.S. Air Force. The Government has certain rights in the invention.

BACKGROUND

Current tools for identification of lung diseases include chest x-rays, lung function tests (i.e. spirometry), sputum cytology, and microbiological tests, which often have poor specificity. In some instances, there is delay in appropriate treatment due to testing time. For example, pathogen identification and antimicrobial susceptibility testing (AST) to inform treatment at the point of care, such as microbiological cultures from sputum and blood, require 1-2 days (see, e.g., Lagier et al., Clin. Microbiol. Rev. 28, 208-236 (2015)) and, for slow-growing pathogens such as *Mycobacterium tuberculosis*, up to weeks (see, e.g., Pfyffer et al., J. Clin. Microbiol. 50, 4188-4189 (2012)). In the interim, patients are prescribed broad-spectrum antibiotics despite the possibility of a non-bacterial cause. Unnecessary antibiotic use contributes to the rise of drug-resistance as well as potential dysbiosis of the patient microbiome (see, e.g., Llor et al., Ther. Adv. Drug Saf. 5, 229-241 (2014)). Furthermore, delays in implementing correct treatment increase risk for infection-associated morbidity or mortality (see, e.g., Weiss et al., Crit Care Med 42, 2409-2417 (2014); Gaieska et al., Crit. Care Med. 38, 1045-1053 (2010)).

SUMMARY

To accelerate pathogen, or other disease or status, identification, a diagnostic platform has been engineered that comprises inhalable, multiplexable nanosensors that can be tuned to release synthetic volatile reporters into the breath in response to specific pathogen-associated (or other disorder) proteases and host proteases upregulated in the lung during infection. The goal of this technology is to leverage aberrant proteolytic activity for pathogen ID, lung disease identification, or a combination thereof via a breath test (FIG. 1).

Thus, in some aspects, the disclosure relates to methods and compositions for identification of pathogenic infections or other diseases in patients using an inhalable nanosensor having a volatile reporter. The disclosure is based, in part, on synthetic biomarkers (e.g., inhalable nanosensors) that are capable of distinguishing (e.g., classifying) different infectious agents in a subject by examining the effect of those agents on a synthetic volatile reporter.

In some aspects a nanosensor comprising a scaffold linked to a synthetic volatile reporter attached to an enzymatic substrate, wherein the volatile reporter is capable of being released from the nanosensor when exposed to an enzyme present in a subject is provided.

In some embodiments the scaffold comprises a high molecular weight protein, a high molecular weight polymer, or a nanoparticle, optionally wherein the protein, polymer or nanoparticle is greater than about 40 kDa. In other embodiments the scaffold comprises a multi-arm polyethylene glycol molecule (multi-arm PEG), optionally wherein the multi-arm PEG comprises 2-20 arms. The multi-arm PEG in some embodiments has a total molecular weight greater than 40 kDa.

In some embodiments, the scaffold is a high molecular weight scaffold that comprises a biological macromolecule, a synthetic macromolecule, or a particle. In some embodiments, the biological macromolecule is a protein, lipid, carbohydrate, or a nucleic acid. In some embodiments, the synthetic macromolecule is a synthetic polymer. In some embodiments, the particle is a nanoparticle or a microparticle. In some embodiments, the scaffold has a total molecular weight greater than 40 kDa In some embodiments the scaffold is linked to a single enzyme-specific substrate. In other embodiments the scaffold is linked to 2 to 20 different enzyme-specific substrates.

In some embodiments each enzyme-specific substrate comprises an infectious agent substrate, optionally wherein the enzyme-specific substrate is cleaved by an enzyme associated with an infection in a subject.

In other embodiments the scaffold comprises a single volatile reporter or multiple volatile reporters.

In some embodiments, the synthetic volatile reporter comprises at least one perfluorocarbon.

In some embodiments, the perfluorocarbon has the chemical formula $CF_3(CF_2)_xCH_2NH_2$.

In some instances, the perfluorocarbon is pentafluoropropylamine (PFP) or heptafluorobutylamine (HFB).

In some embodiments the enzyme-specific substrate is a peptide, nucleic acid, glycan, or lipid.

In some embodiments, the enzyme is present in the lung of a subject.

In other aspects, the invention is a method comprising detecting in a breath sample obtained from a subject that has been administered a nanosensor of the present disclosure, one or more volatile reporters that have been released from one or more nanosensors when exposed to an enzyme present in the subject. In some embodiments the detecting comprises mass spectrometry, ion mobility spectroscopy, or any combination thereof. In other embodiments the administration of the nanosensor is by inhalation.

Further aspects of the present disclosure provide a method comprising: (a) detecting in a breath sample obtained from a subject that has been administered a nanosensor of the present disclosure one or more volatile reporters that have been released from one or more nanosensors when exposed to an enzyme present in the subject; and (b) classifying the subject as having an infection upon detection of the one or more volatile reporters.

Another aspect of the present disclosure provides a method comprising: (a) administering any nanosensor described herein to a subject; and (b) detecting in a breath sample obtained from the subject one or more volatile reporters that have been released from one or more nanosensors when exposed to an enzyme present in the subject.

In some embodiments, the subject has, is suspected of having, or is at risk for an infectious disease. In some embodiments, the infectious disease is pneumonia.

In some embodiments, an increase in the presence of the volatile reporter relative to the level of the volatile reporter from a healthy subject is indicative of the subject having a disease.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF DRAWINGS

FIG. 2A is schematic showing a non-limiting example of the general structure of protease nanosensors. Protease-specific release of volatile reporters is programmed through peptide substrate sequence. FIG. 2B is a schematic showing volatile reporter signal resulting from cleavage of the peptide linker by the protease of interest (release of reporters (represented by circles) in top panel) and absence of signal in the presence of a protease that does not cleave the peptide linker (no release of reporter in bottom panel). FIG. 2C is a heatmap showing cleavage of NE sensors by different proteases found in the lung. PFP and HFB are 2 different perfluorocarbons reporters. FIG. 2D shows Michaelis-Menten kinetics of substrate cleavage derived from vapor mass-spectrometry measurement of the volatile reporter.

FIG. 3A shows a timeline of the experiment. Mice were infected with P. aeruginosa to cause neutrophil recruitment to the lungs to increase NE levels to determine nanosensor response to physiologic levels of NE in healthy and infected mice. FIG. 3B is a graph showing ELISA measurements of supernatant from lung homogenates. FIG. 3C is a graph showing the reporter release rate during incubation of NE nanosensors with lung homogenates from healthy controls and infected mice as measured by vapor analysis mass-spectrometry.

FIG. 4A is a schematic of a non-limiting example of a breath collection method. After nanosensor inhalation, mice were placed in the barrel of a 120 cc syringe. The syringe was sealed for 2 min to build up reporter levels in the headspace. After 2 min, the stopcock valve was opened and 50 cc headspace was displaced into 5 EXETAINER™ vials (10 cc headspace per vial). This was repeated 10 times for a 20 min total breath collection. FIG. 4B shows total reporter counts in Exetainers™ over the 20 min breath collection period. A 2-way ANOVA indicates breath from infected mice have significantly greater reporter levels than breath from healthy controls ($p<0.05$) with no significant difference due to time or interaction of disease state and time. FIG. 4C are optical images taken of the lungs using a LI-COR imager to assess bacteria and nanosensor distribution after inhalation. FIG. 4D is a graph showing the calculated effect sizes to assess the size of the difference between total reporter counts in the breath of infected and healthy mice. At 16 min (arrow), reporter levels showed the largest effect size while demonstrating perfect distinction between healthy and infected mice. FIG. 4E is a graph showing analysis of breath samples from the 16 min timepoint shows infected mice had 3-fold greater reporter levels than healthy controls ($p=0.0035$).

FIGS. 100A-10C include data showing breath signal in healthy control mice versus infected mice. FIG. 10C shows ROC curve for detecting infected mice by breath signal at 10 min after 10 µM dose inhalation.

FIG. 11A shows that nanosensors produced higher breath signal than peptide substrates in infected mice. FIG. 11B shows that SNR was maintained at >1.0 for ~3× longer.

FIG. 13 shows a list of volatile reporter candiates identified from FDA- and FEMA-approved food flavorings.

FIG. 14 shows a non-limiting set of extracellular bacterial protease targets and substrates. + indicates cleavage site for substrates. Z. Boc. and Suc are protective groups. AM C indicates 7-amino-4-methylcoumarin (a fluorophore reporter for peptide cleavage). FIG. 14 includes the following sequences: Z-AG+LA (SEQ ID NO: 5); LGG+GA (SEQ ID NO: 1); FGAK-AM C (SEQ ID NO: 6); IAAG-AM C (SEQ ID NO: 7); IAKD-AM C (SEQ ID NO: 8); and Suc-LLVY-AM C (SEQ ID NO: 9).[5] Gaieska et al., Crit. Care Med. 38, 1045-1053 (2010).[7] Bascomb et al., Clin. Microbiol. Rev. 11, 318-340 (1998);[46] Haiko et al., J Bacteriol. 192, 4553-4561 (2010);[47] Morihara et al., Methods Enzymol. 248, 242-253 (1995);[48] Mccarter et al., J Bacteriol. 186, 5919-5925 (2004);[49] Thomassin et. al., Infect. Immun. 80, 483-492 (2012);[50] Johnson et al., J Mol Biol 389, 559-574 (2010);[51] Vessillier et al., Eur J Biochem 268, 1049-1057 (2001);[52] Shibuya et al., Biochim Biophys Acta. 1077, 316-324 (1991);[53] Handbook of Proteolytic Enzymes. (Academic Press, 2013);[54] Shaw et al., Microbiology 150, 217-228 (2018);[55] Holliday et al., J Clin Microbiol 37, 1190-1192 (1999);[56] Wildeboer et al., Anal. Biochem. 384, 321-328 (2009);[58] Kalinska et al., Biochimie 94, 318-327 (2012).

DETAILED DESCRIPTION

Figure 1:
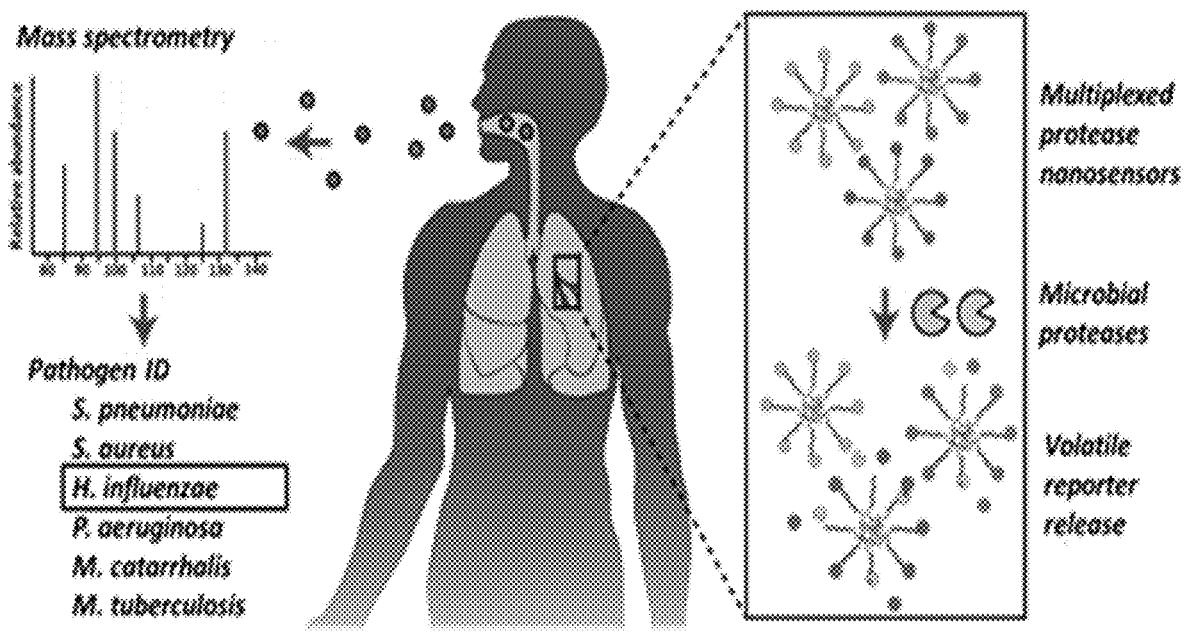
FIG. 1 is a schematic of breathalyzer test for rapid pathogen identification in respiratory infection. Pathogen-specific proteolytic activity triggers release of volatile reporters. Volatile reporter signatures enable identification of bacterial pathogen.

Diagnosing or monitoring disease using breath analysis is attractive because it is non-invasive. However, the use of endogenous volatile organic compounds (VOCs, also referred to herein as volatile reporters) as breath biomarkers is limited due to numerous reasons. VOCs detected in the breath may also be present in the environment, food, or personal care products at similar levels and, thus, confound breath measurements (see, e.g., Kwak et al., Curr Pharm Biotechnol 12, 1067-74 (2011)). Large inter-individual variations in breath volatiles also makes it difficult to find a universal breath biomarker (see, e.g., Phillips et al., J. Chromatogr. B 729, 75-88 (1999)). In an analysis of breath samples from fifty subjects, out of the 3481 different VOCs that were identified, only 27 "common core" VOCs were observed in all fifty subjects (see, e.g., Phillips et al., J. Chromatogr. B 729, 75-88 (1999)). Furthermore, endogenous VOCs are present at very low levels, and, thus, require highly sensitive measurement technologies such as mass spectrometry or preconcentration steps before analysis. Additionally, the diversity of VOCs and their varied concentrations have prevented rapid standardization of breath collection methods and sample analysis (see, e.g., Herbig et al., J Breath Res 8, 1-11 (2014)). Therefore, there are numerous limitations to the use of endogenous VOCs. Without being bound by a particular theory, the nanosensors described herein obviate some of the challenges associated with endogenous VOCs by releasing synthetic VOCs as reporters for disease.

Synthetic volatile compounds such as perfluorocarbons (PFCs) do not exist in the human body or in the environment and, therefore, breath levels cannot be confounded by exogenous sources. Furthermore, synthetic VOC reporters would eliminate the need to identify a universal breath biomarker across all populations and focus standardization of breath collection and analysis to specific classes of volatile compounds. To drive differential reporter levels in breath from healthy and diseased patients, sensors could leverage upregulated enzymatic activity in the diseased tissue microenvironment as previously demonstrated in urinary reporter diagnostics (see, e.g., Kwong et al., Nat. Biotechnol. 31, 63-70 (2013); Kwong et al., PNAS 112, 21-24 (2015); Dudani et al., ACS Nano 9, 11708-11717 (2015)).

Though promising in concept, a number of potential pitfalls existed with this technology including the following: (1) difficult chemistry for attaching VOC reporters to enzymatic substrates in such a way as to allow for release of VOC in its original, volatile form (2) low reporter release due to limited nanosensor access to enzymes as a result of nanosensor administration or phagocytosis of nanosensors by immune cells (3) low enzymatic turnover rate that does not allow for accumulation of measurable reporter levels in the breath and (4) potential partitioning of the released VOC reporter into the blood or tissue instead of the air. It has been demonstrated herein that these potential obstacles can be overcome using the nanosensors of the invention.

It has been demonstrated that a nanosensor that releases a synthetic volatile reporter in the presence of neutrophil elastase (NE), a serine protease secreted by neutrophils at the site of infection may be synthesized. NE has many roles in infection including intracellular and extracellular bacterial killing, degradation of bacterial virulence factors, and modulation of immune response via processing of chemokines and cytokines and activation of specific cell-surface receptors (see, e.g., Pham, Nat. Rev. Immunol. 6, 541-550 (2006)). Using real-time vapor analysis mass spectrometry (see, e.g., Ong et al., Anal. Chem. 89, 6482-6490 (2017)), it was shown that rapid reporter release from the nanosensor is triggered specifically by NE in vitro. In ex vivo studies, greater reporter release was demonstrated when nanosensors were added to infected lung homogenates versus healthy lung homogenates. Furthermore, perfect distinction between mice with and without bacterial pneumonia were shown based on reporter levels in the breath as early as 12 minutes after nanosensor inhalation. With the appropriate choice of enzymatic substrate, volatile reporter, delivery route, animal model, and breath collection method and analysis, the feasibility in the synthesis of nanoscale sensors with volatile reporters was demonstrated and their application in surveying proteolytic activity in the lung for diagnostic application was also demonstrated. The number of nanosensors may be expanded for multiplexing to generate volatile reporter signatures for specific bacterial respiratory pathogens such as *Mycobacterium tuberculosis, Streptococcus pneumoniae, Haemophilus influenzae, Pseudomonas aeruginosa*, etc.

Figure 2A:
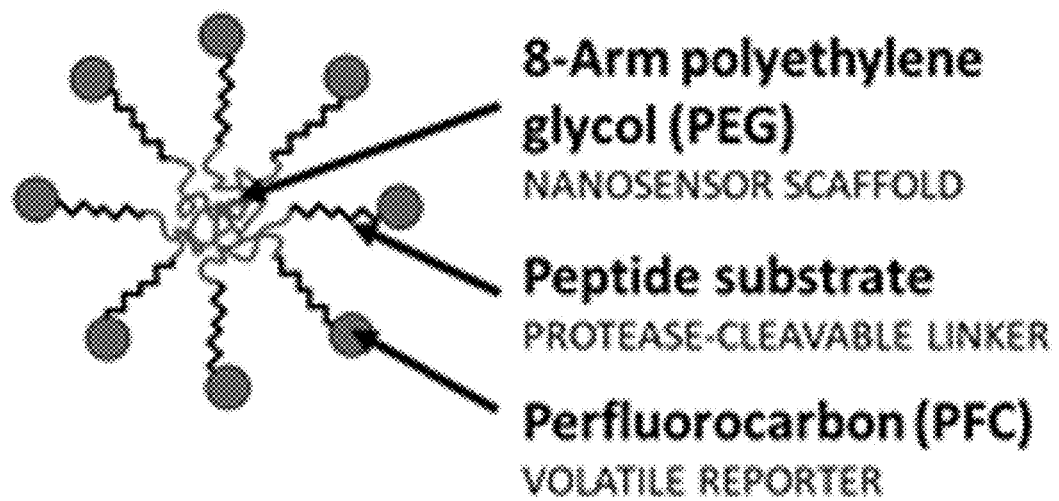
FIGS. 2A-2D show neutrophil elastase (NE) nanosensor structure and characterization.
Figure 2B:
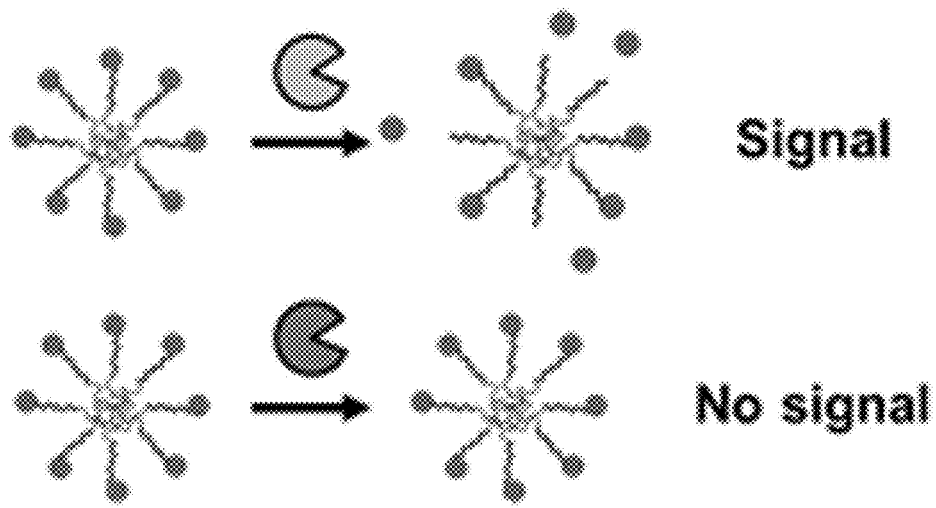

Nanosensors have a modular structure, which allows each sensor to be engineered to release reporters in response to specific enzymes. Broadly, nanosensors are comprised of a nanoparticle scaffold to which volatile reporters are attached via an enzymatic substrate (e.g. peptides, glycans, lipids, nucleic acids) (FIG. 2A). Without being bound by a particular theory, attachment of the volatile reporter to the nanoparticle scaffold prevents the partition of the reporter into gas phase, and the reporter is, thus, undetectable by volatile compound detection methods. After administration into the lung, the targeted enzyme hydrolyzes the bond between the substrate and the reporter, allowing the reporter to be released into the breath in its detectable, volatile form (FIG. 2B).

Perfluorocarbons (PFCs) were identified as suitable reporter molecules due to their inertness, high volatility, low limit of detection via mass-spectrometry, absence of naturally-occurring fluorinated compounds in the body, and precedence for biomedical use (e.g., component in microbubble contrast agents for ultrasound imaging (see, e.g., Unger et al., Adv Drug Deliv Rev 56, 1291-1314 (2004)), oxygen carriers for blood substitutes (Spahn, Crit. care 3, 93-97 (1999)), and use in vitreoretinal surgeries (see, e.g., Yu et al., Biomed Res. Int. 2014, (2014)). Furthermore, amine-functionalized PFCs ($CF_3(CF_2)_xCH_2NH_2$), which are commercially available, can be easily attached to the C-terminus of peptide substrates via a protease-cleavable amide bond for release of the original volatile PFC. Any suitable method known in the art or described herein may be used to assemble a nanosensor comprising a synthetic volatile reporter (e.g., a synthetic volatile compound including a perfluorocarbon). See, e.g., the examples below.

Fluorogenic and chromogenic substrates are currently used in clinical laboratory assays and are multiplexed to identify bacteria down to the species level (see, e.g., Bascomb et al., Clin. Microbiol. Rev. 11, 318-340 (1998)). Without being bound by a particular theory, the nanosensors described herein comprise synthetic volatile reporters, which can be released in the presence of an enzyme and the volatile reporter can be read in the breath eliminating the need for an additional culturing step.

Nanosensors Enable Rapid Pathogen Identification

Nanosensors produce disease-distinguishing reporter signal in the breath within 20 min after inhalation. Testing time is significantly shortened by leveraging pre-existing bacterial growth within the host, thus, eliminating the need for culture. In contrast, culture-based methods are the primary means of pathogen identification in the clinical laboratory and require ~1-2 days, and for slower-growing pathogens, up to weeks (Laupland et al., Can J Infect Dis Med Microbiol 24, 125-128 (2013)). Bacteria from patient samples are grown on solid/liquid media and are identified based on phenotypic observations such as colony and cellular morphology, growth conditions, and biochemical testing for carbohydrate use and enzymatic activity (see, e.g., Laupland et al., Can J Infect Dis Med Microbiol 24, 125-128 (2013); Baron, Medical Microbiology (ed. Baron, S.) (1996)). Some examples of commercially available biochemical testing materials include OXI/FERM™ tubes and ENTEROTUBES™ (Becton Dickinson), which are compartmentalized tubes in which each compartment contains a chromogenic indicator for a specific reaction. After inoculation with the culture, tubes are incubated for 1-2 days and subsequently assessed for color changes corresponding to specific bacterial species.

Nanosensors Release Synthetic Reporters not Found in the Human Body

Perfluorocarbons are not found naturally in the body and in the environment. Therefore, any perfluorocarbon measured in the breath is solely due to reporter release from the nanosensor, eliminating concerns of contaminants from the environment, diet, etc. Numerous reports have proposed the use of endogenous breath biomarkers for identifying infectious agents (see, e.g., Zhu et al., J Breath Res 7, 1-15 (2013)) and diagnosing conditions such as liver cirrhosis (see, e.g., Fernández et al., EBIOM 2, 1243-1250 (2015)) and lung cancer (see, e.g., Krilaviciute et al., Oncotarget 6, 38643-38657 (2015)). However, the use of endogenous volatiles is difficult due to the fact that many putative markers are present in the environment at even higher levels and the large variability in baseline levels from person to person (see, e.g., Kwak et al., Curr Pharm Biotechnol 12, 1067-74 (2011)). These problems are eliminated by using a purely synthetic volatile reporter in the nanosensor.

Nanosensor Modularity

Nanosensors were designed to be modular so that volatile reporter release can be tuned to specific proteases by modification of the peptide linker sequence. In addition, peptide linkers may be replaced by other classes of substrates such as glycans, lipids, or nucleic acids to query glycosidase, lipase, and DNAse/RNAse activity, respectively. Different classes of volatile organic compounds may also be used in place of perfluorocarbon reporters. See, e.g., FIG. 13. The interchangeability of the linker as well as reporter provides a number of possible nanosensor configurations for multiplexing.

Nanosensor Multiplexing Enables Broad Spectrum Pathogen Identification

Breathalyzer tests are rapid, non-invasive, and cost-effective, making them ideal point-of-care diagnostic tools in both resource-rich and resource-poor settings. To date, there are two breathalyzer tests that are used in the clinic to detect bacterial activity: the *H. pylori* breath test measuring urease activity (see, e.g., Berger, B M J 324, 1263 (2002)) and hydrogen breath test for diagnosing small intestinal bacterial overgrowth (SIBO) (Ghosal et al., J Neurogastroenterol Motil 17, 312-317 (2011)). As of yet, no breath test exists that is able to ID a panel of bacterial pathogens. To enable identification of bacteria at the species level, a multiplexed system of protease-responsive nanosensors with orthogonal volatile reporters may be engineered to generate a proteolytic fingerprint for key bacterial pathogens. As opposed to the use of one nanosensor, the ability to multiplex provides the ability to differentiate between different bacterial pathogens with greater accuracy. Improved diagnostic accuracy of liver fibrosis (Kwong et al., Nat. Biotechnol. 31, 63-70 (2013)), lung adenocarcinoma, and prostate cancer have previously been demonstrated through multiplexing nanosensors with urinary reporters.

Nanosensors Enable Point-of-Care Testing (POCT)

Additional methods for pathogen identification in the clinical laboratory include nucleic acid-based assays to amplify target DNA/RNA (Laupland et al., Can J Infect Dis Med Microbiol 24, 125-128 (2013)) and mass spectrometry (see, e.g., Murray, JMDI 14, 419-423 (2012)). However, these methods in addition to culture-based methods require technical expertise in sample preparation and instrumentation in contrast to a simple breath test after nanosensor inhalation. While nanosensor validation was completed using a real-time vapor mass-spectrometer, portable handheld gas detectors and electronic noses made up of multisensor arrays (see, e.g., Wilson et al., 5099-5148 (2009). doi:10.3390/s90705099) exist and can be modified to detect reporter molecules from our nanosensors. Therefore, breath tests utilizing our nanosensors can be used for point-of-care testing (POCT) outside of the clinical laboratory setting without any bulky instrumentation. This would enable more rapid, directed therapies at the bedside in place of empirical treatment which is the current standard of care for respiratory infections. Furthermore, a breath test is simple to implement, enabling potential use in developing countries where acute respiratory infections are a significant contributor to childhood mortaility (Berman, Rev. Infect. Dis. 13, S454-S462 (1991)).

Volatile-releasing nanosensors have many diagnostic applications. They can be used for rapid bacterial, viral, fungal, parasitic pathogen identification in infections with possible strain-level differentiation that could be useful for identifying drug resistance. In the body, volatile molecules partition from tissues into circulation and subsequently into the alveolar space in the lung for release in breath (see, e.g., Turner et al., J Breath Res 11, (2017)). Therefore, protease-responsive materials that release volatile organic compounds (VOCs) can potentially be applied beyond the lung setting (e.g. GI tract, blood compartment). Furthermore, due to the ubiquitous nature of proteases in living systems, these nanosensors may be used to query proteases in a broad range of diseases in which there is aberrant protease activity (e.g. cancer, inflammation (Salaun et al., PLoS One 10, e0132960 (2015); El-Badrawy et al., J Bronchol. Interv Pulmonol 21, 327-334 (2014))). Thus, the proposed nanosensors here have extensive value and application beyond that of infectious disease diagnostics.

Synthetic Volatile Reporters

As used herein, a volatile reporter is capable of vaporizing at room temperature. In some instances, a volatile reporter is capable of partitioning from liquid phase into headspace. In some instances, a volatile reporter is capable of phase transition from liquid to gas. A synthetic volatile reporter may comprise a volatile organic compound (VOC). A volatile reporter may be naturally produced by a cell or subject and may be referred to as an endogenous volatile reporter. In some instances, a volatile reporter is not naturally produced by a cell or organism. As used herein, a synthetic volatile reporter is a volatile reporter that is not naturally produced by a cell or a subject. In some instances, the subject is a human.

A volatile reporter may comprise at least one 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 30, at least 40, at least 50, at least 60, at least 70, at least 80, at least 90, or at least 100 volatile organic compounds. In some instances, the volatile organic compound is a perfluorocarbon.

As a non-limiting example, a synthetic volatile reporter may comprise a perfluorocarbon (PFC). PFCs are fluorinated carbon compounds. In some instances, a PFC comprises a carbon-fluorine bond. In some embodiments, a PFC comprising is a perfluoroalkane.

There are at least four types of PFCs. In some instances, PFCs are cyclic, branched, or linear, completely fluorinated alkanes; cyclic, branched, or linear, completed fluorinated ethers, with no unsaturations; cyclic, branched, or linear, completely fluorinated tertiary-amines with no unsaturations; or sulfur containing perfluorocarbons with no unsaturations and with sulfur bonds only to carbon and fluoride). In some embodiments, the perfluorocarbon has the chemical formula $CF_3(CF_2)_xCH_2NH_2$. In some instances, x in the chemical formula $CF_3(CF_2)_xCH_2NH_2$ is 1, 2, 3, 4, 5, 6, 7, 8, 9, 10, 11, 12, 13, 14, 15, 16, 17, 18, 19, 20, 25, 30, 35, 40, 50, 60, 70, 80, 90, or 100, including any values in between. In some instances, the perfluorocarbon is pentafluoropropylamine or heptafluorobutylamine. In some instances, the VOCs are biocompatible and highly volatile (have a high vapor pressure).

In some instances, the volatile organic compounds (VOCs) comprise an amine. In some instances the amine is useful for conjugation to a scaffold.

Additional classes of VOCs include food flavorings. For example, the food flavings may comprise an alcohol or a thiol. FIG. 13 shows a non-limiting list of volatile reporter candiates from the Federal Drug Administration (FDA)- and flavor extract manufacturers association (FEMA)-approved food flavorings. In some instances, a VOC is methanethiol, 2-Propene-1-thiol, 2-Proanethiol, 1-ropanethiol, 2-Methyl-1-propanethiol, 1-Butanethiol, 2-Pentanethiol, 3-Methyl-1-butanethiol, 1-Pentanethiol, ethanol, propanol, isopropyl alcohol, isobutyl alcohol, butyl alcohol, 2-Methyl-3-buten-2-ol, 1-Penten-3-ol, Isoamyl alcohol, or amyl alcohol. In some instances, a VOC may comprise a sulfur, hydroxyl group, or any combination thereof and have a high vapor pressure and a low boiling point. In some instances, the VOCs are not bio-orthogonal and may have naturally produced metabolite counterparts. In contrast, perfluorocarbons may be considered bio-orthogonal, as they are not naturally produced in the human body.

Any suitable method known in the art or described herein may be used to detect a volatile reporter. For example, a VOC in a volatile reporter may be detected and detection of a VOC may comprise gas chromatography, mass spectrometry, gas chromatography-mass spectrometry (GC-MS), chemiluminescence, use of electronic noses, optical absorption spectroscopy, ion mobility spectroscopy, use of different types of gaseous sensors, or any combination thereof. See, e.g., Sethi et al., Clin Microbiol Rev. 2013 July; 26(3):462-75.

Scaffolds

The enzyme nanosensor comprises a modular structure having a scaffold linked to an enzyme-specific substrate. A modular structure, as used herein, refers to a molecule having multiple domains.

The scaffold may include a single type of substrate, such as, a single type of enzyme-specific substrate, or it may include multiple types of different substrates. For instance each scaffold may include a single (e.g., 1) type of substrate or it may include 2-1,000 different substrates, or any integer therebetween. Alternatively, each scaffold may include greater than 1,000 different substrates. Multiple copies of the enzyme nanosensor are administered to the subject. In some embodiments, a composition comprising a plurality of different nanosensors may be administered to a subject to determine whether multiple enzymes and/or substrates are present. In that instance, the plurality of different nanosensors includes a plurality of volatile reporters, such that each substrate is associated with a particular volatile reporter.

The scaffold may serve as the core of the nanosensor. A purpose of the scaffold is to serve as a platform for the substrate and enhance delivery of the nanosensor to the subject. As such, the scaffold can be any material or size as long as it can enhance delivery and/or accumulation of the nanosensors to the subject. Preferably, the scaffold material is non-immunogenic, i.e. does not provoke an immune response in the body of the subject to which it will be administered. Non-limiting examples of scaffolds, include, for instance, compounds that cause active targeting to tissue, cells or molecules, microparticles, nanoparticles, aptamers, peptides (RGD, iRGD, LyP-1, CREKA, etc.), proteins, nucleic acids, polysaccharides, polymers, antibodies or antibody fragments (e.g., herceptin, cetuximab, panitumumab, etc.) and small molecules (e.g., erlotinib, gefitinib, sorafenib, etc.).

In some aspects, the disclosure relates to the discovery that delivery to a subject by inhalation is enhanced by nanosensors having certain polymer scaffolds (e.g., poly (ethylene glycol) (PEG) scaffolds). Polyethylene glycol (PEG), also known as poly(oxyethylene) glycol, is a condensation polymer of ethylene oxide and water having the general chemical formula $HO(CH_2CH_2O)[n]H$. Generally, a PEG polymer can range in size from about 2 subunits (e.g., ethylene oxide molecules) to about 50,000 subunits (e.g., ethylene oxide molecules. In some embodiments, a PEG polymer comprises between 2 and 10,000 subunits (e.g., ethylene oxide molecules).

A PEG polymer can be linear or multi-armed (e.g., dendrimeric, branched geometry, star geometry, etc.). In some embodiments, a scaffold comprises a linear PEG polymer. In some embodiments, a scaffold comprises a multi-arm PEG polymer. In some embodiments, a multi-arm PEG polymer comprises between 2 and 20 arms. Multi-arm and dendrimeric scaffolds are generally described, for example by Madaan et al. *J Pharm Bioallied Sci.* 2014 6(3): 139-150.

Additional polymers include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxyethyl cellulose, cellulose triacetate, cellulose sulphate sodium salt, poly(methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride and polystyrene.

Examples of non-biodegradable polymers include ethylene vinyl acetate, poly(meth) acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), poly(caprolactone), poly(hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. In some embodiments the polymers are polyesters, polyanhydrides, polystyrenes, polylactic acid, polyglycolic acid, and copolymers of lactic and glycoloic acid and blends thereof.

PVP is a non-ionogenic, hydrophilic polymer having a mean molecular weight ranging from approximately 10,000 to 700,000 and the chemical formula $(C_6H_9NO)[n]$. PVP is also known as poly[1-(2-oxo-1-pyrrolidinyl)ethylene], POVIDONE™, POLYVIDONE™, RP 143™, KOLLIDON™, PEREGAL ST™, PERISTON™, PLASDONE™, PLASMOSAN™, PROTAGENT™, SUBTOSAN™, and VINISIL™. PVP is non-toxic, highly hygroscopic and readily dissolves in water or organic solvents.

Polyvinyl alcohol (PVA) is a polymer prepared from polyvinyl acetates by replacement of the acetate groups with hydroxyl groups and has the formula $(CH_2CHOH)[n]$. Most polyvinyl alcohols are soluble in water.

PEG, PVA and PVP are commercially available from chemical suppliers such as the Sigma Chemical Company (St. Louis, Mo.).

In certain embodiments the particles may comprise poly(lactic-co-glycolic acid) (PLGA).

In some embodiments, a scaffold (e.g., a polymer scaffold, such as a PEG scaffold) has a molecular weight equal to or greater than 40 kDa. In some embodiments, a scaffold is a nanoparticle (e.g., an iron oxide nanoparticle, IONP) that is between 10 nm and 50 nm in diameter (e.g. having an average particle size between 10 nm and 50 nm, inclusive). In some embodiments, a scaffold is a high molecular weight protein, for example an Fc domain of an antibody.

As used herein the term "particle" includes nanoparticles as well as microparticles. Nanoparticles are defined as particles of less than 1.0 µm in diameter. A preparation of nanoparticles includes particles having an average particle size of less than 1.0 µm in diameter. Microparticles are particles of greater than 1.0 µm in diameter but less than 1 mm. A preparation of microparticles includes particles having an average particle size of greater than 1.0 µm in diameter. The microparticles may therefore have a diameter of at least 5, at least 10, at least 25, at least 50, or at least 75 microns, including sizes in ranges of 5-10 microns, 5-15 microns, 5-20 microns, 5-30 microns, 5-40 microns, or 5-50 microns. A composition of particles may have heterogeneous size distributions ranging from 10 nm to mm sizes. In some embodiments the diameter is about 5 nm to about 500 nm. In other embodiments, the diameter is about 100 nm to about 200 nm. In other embodiment, the diameter is about 10 nm to about 100 nm.

The particles may be composed of a variety of materials including iron, ceramic, metallic, natural polymer materials (including lipids, sugars, chitosan, hyaluronic acid, etc.), synthetic polymer materials (including poly-lactide-coglycolide, poly-glycerol sebacate, etc.), and non-polymer materials, or combinations thereof.

The particles may be composed in whole or in part of polymers or non-polymer materials. Non-polymer materials, for example, may be employed in the preparation of the particles. Exemplary materials include alumina, calcium carbonate, calcium sulfate, calcium phosphosilicate, sodium phosphate, calcium aluminate, calcium phosphate, hydroxyapatite, tricalcium phosphate, dicalcium phosphate, tricalcium phosphate, tetracalcium phosphate, amorphous calcium phosphate, octacalcium phosphate, and silicates. In certain embodiments the particles may comprise a calcium salt such as calcium carbonate, a zirconium salt such as zirconium dioxide, a zinc salt such as zinc oxide, a magnesium salt such as magnesium silicate, a silicon salt such as silicon dioxide or a titanium salt such as titanium oxide or titanium dioxide. A number of biodegradable and non-biodegradable biocompatible polymers are known in the field of polymeric biomaterials, controlled drug release and tissue engineering (see, for example, U.S. Pat. Nos. 6,123,727; 5,804,178; 5,770,417; 5,736,372; 5,716,404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera; U.S. Pat. No. 5,019,379 to Domb; U.S. Pat. No. 5,010,167 to Ron; U.S. Pat. No. 4,946,929 to d'Amore; and U.S. Pat. Nos. 4,806,621; 4,638,045 to Kohn; see also Langer, Acc. Chem. Res. 33:94, 2000; Langer, J. Control Release 62:7, 1999; and Uhrich et al., Chem. Rev. 99:3181, 1999; all of which are incorporated herein by reference).

The scaffold may be composed of inorganic materials. Inorganic materials include, for instance, magnetic materials, conductive materials, and semiconductor materials. In some embodiments, the scaffold is composed of an organic material.

In some embodiments, the particles are porous. A porous particle can be a particle having one or more channels that extend from its outer surface into the core of the particle. In some embodiments, the channel may extend through the particle such that its ends are both located at the surface of the particle. These channels are typically formed during synthesis of the particle by inclusion followed by removal of a channel forming reagent in the particle. The size of the pores may depend upon the size of the particle. In certain embodiments, the pores have a diameter of less than 15 microns, less than 10 microns, less than 7.5 microns, less than 5 microns, less than 2.5 microns, less than 1 micron, less than 0.5 microns, or less than 0.1 microns. The degree of porosity in porous particles may range from greater than 0 to less than 100% of the particle volume. The degree of porosity may be less than 1%, less than 5%, less than 10%, less than 15%, less than 20%, less than 25%, less than 30%, less than 35%, less than 40%, less than 45%, or less than 50%. The degree of porosity can be determined in a number of ways. For example, the degree of porosity can be determined based on the synthesis protocol of the scaffolds (e.g., based on the volume of the aqueous solution or other channel-forming reagent) or by microscopic inspection of the scaffolds post-synthesis.

The plurality of particles may be homogeneous for one or more parameters or characteristics. A plurality that is homogeneous for a given parameter, in some instances, means that particles within the plurality deviate from each other no more than about +/−10%, preferably no more than about +/−5%, and most preferably no more than about +/−1% of a given quantitative measure of the parameter. As an example, the particles may be homogeneously porous. This means that the degree of porosity within the particles of the plurality differs by not more than +/−10% of the average porosity. In other instances, a plurality that is homogeneous means that all the particles in the plurality were treated or processed in the same manner, including for example exposure to the same agent regardless of whether every particle ultimately has all the same properties. In still other embodiments, a plurality that is homogeneous means that at least 80%, preferably at least 90%, and more preferably at least 95% of particles are identical for a given parameter.

The plurality of particles may be heterogeneous for one or more parameters or characteristics. A plurality that is heterogeneous for a given parameter, in some instances, means that particles within the plurality deviate from the average by more than about +/−10%, including more than about +/−20%. Heterogeneous particles may differ with respect to a number of parameters including their size or diameter, their shape, their composition, their surface charge, their degradation profile, whether and what type of agent is comprised by the particle, the location of such agent (e.g., on the surface or internally), the number of agents comprised by the particle, etc. The disclosure contemplates separate synthesis of various types of particles which are then combined in any one of a number of pre-determined ratios prior to contact with the sample. As an example, in one embodiment, the particles may be homogeneous with respect to shape (e.g., at least 95% are spherical in shape) but may be heterogeneous with respect to size, degradation profile and/or agent comprised therein.

Particle size, shape and release kinetics can also be controlled by adjusting the particle formation conditions. For example, particle formation conditions can be optimized to produce smaller or larger particles, or the overall incubation time or incubation temperature can be increased, resulting in particles which have prolonged release kinetics.

The particles may also be coated with one or more stabilizing substances, which may be particularly useful for long term depoting with parenteral administration or for oral delivery by allowing passage of the particles through the stomach or gut without dissolution. For example, particles intended for oral delivery may be stabilized with a coating of a substance such as mucin, a secretion containing mucopolysaccharides produced by the goblet cells of the intestine, the submaxillary glands, and other mucous glandular cells.

To enhance delivery the particles may be incorporated, for instance, into liposomes, virosomes, cationic lipids or other lipid based structures. The term "cationic lipid" refers to lipids which carry a net positive charge at physiological pH. Such lipids include, but are not limited to, DODAC, DOTMA, DDAB, DOTAP, DC-Chol and DMRIE. Additionally, a number of commercial preparations of cationic lipids are available. These include, for example, LIPOFEC-TIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS in ethanol from Promega Corp., Madison, Wis., USA). A variety of methods are available for preparing liposomes e.g., U.S. Pat. Nos. 4,186,183, 4,217,344, 4,235,871, 4,261,975, 4,485,054, 4,501,728, 4,774,085, 4,837,028, 4,946,787; and PCT Publication No. WO 91/17424. The particles may also be composed in whole or in part of GRAS components. i.e., ingredients are those that are Generally Regarded As Safe (GRAS) by the US FDA. GRAS components useful as particle material include non-degradable food based particles such as cellulose.

In some embodiments, the scaffold is a high molecular weight scaffold that comprises a biological macromolecule, a synthetic macromolecule, or a particle. In some embodiments, the biological macromolecule is a protein, lipid, carbohydrate, or a nucleic acid. In some embodiments, the synthetic macromolecule is a synthetic polymer. In some embodiments, the particle is a nanoparticle or a microparticle. In some embodiments, the scaffold has a total molecular weight greater than 40 kDa Optionally the scaffold may include a biological agent. In one embodiment, a biological agent could be incorporated in the scaffold or it may make up the scaffold. Thus, the compositions of the invention can achieve two purposes at the same time, the diagnostic methods and delivery of a therapeutic agent. In some embodiments the biological agent may be an enzyme inhibitor. In that instance the biological agent can inhibit proteolytic activity at a local site and the detectable marker can be used to test the activity of that particular therapeutic at the site of action.

Substrates

The enzyme-specific substrate is a portion of the modular structure that is connected to the scaffold. A substrate, as used herein, is the portion of the modular structure that promotes the enzymatic reaction in the subject, causing the release of a detectable marker. The substrate typically comprises an enzyme-sensitive portion (e.g., protease substrate) linked to a detectable marker.

In some instances, the substrate is dependent on enzymes that are active in a specific disease state (e.g., infection). For example, infections are associated with a specific set of enzymes. A nanosensor is designed with one or more substrates that match those of the enzymes expressed by the infectious agent, by the subject in response to the infection or by other diseased tissue. Alternatively, the substrate may be associated with enzymes that are ordinarily present but are absent in a particular disease state. In this example, a disease state would be associated with a lack of signal associated with the enzyme, or reduced levels of signal compared to a normal reference.

An enzyme, as used herein refers to any of numerous proteins produced in living cells that accelerate or catalyze the metabolic processes of an organism. Enzymes act on substrates. The substrate binds to the enzyme at a location called the active site just before the reaction catalyzed by the enzyme takes place. Enzymes include but are not limited to proteases, glycosidases, lipases, heparinases, phosphatases. In some embodiments, the enzyme is present in a lung of a subject.

In some embodiments, a substrate comprises an amino acid sequence that is cleaved by an enzyme (e.g., an enzyme-specific substrate). In some embodiments, the enzyme-specific substrate comprises an amino acid sequence cleaved by a serine protease, cysteine protease, threonine protease, aspartic protease, glutamic protease, or a metalloprotease.

In some instances, the substrate is dependent on enzymes that are active in a specific disease state, including, e.g., lung disease, infectious disease, inflammation, and cancer. See, e.g., Tables 1 and 2 and FIG. 14.

TABLE 1

Non-limiting examples of disease-associated enzymes and substrates.

| Disease | Enzyme | Substrate |
| --- | --- | --- |
| Cancer | MMP | collagens, gelatin, various ECM proteins |
| Cancer | MMP-2 | type IV collagen and gelatin |
| Cancer | MMP-9 | type IV and V collagens and gelatin |
| Cancer | Kallikreins | kininogens, plasminogen |
| Cancer | Cathepsins | broad spectrum of substrates |
| Cancer | plasminogen activator, tPA | Plasminogen |
| Cancer | Urokinase-type plasminogen activator, uPA | Plasminogen |
| Cancer | ADAM (A Diseintegrin And Metalloprotease, also MDC, Adamalysin) | various extracellular domains of transmembrane proteins |
| Pancreatic carcinoma | MMP-7 | various, e.g. collagen 18, FasL, HLE, DCN, IGFBP-3, MAG, plasminogen, other MMPs |
| Pancreatic Cancer | ADAM9, ADAM15 | various extracellular domains of transmembrane proteins |
| Prostate adenocarcinoma | Matriptase, a type II transmembrane serine protease | unspecific, cleaves after Lys or Arg residues |
| Prostate cancer | Kallikrein 3 | kininogens, plasminogen |
| Prostate cancer | ADAM15 | various extracellular domains of transmembrane proteins |
| Ovarian carcinoma | Kallikrein 6 | kininogens, plasminogen |
| Epithelial-derived tumors (breast, prostate, ovarian, colon, oral) | Matriptase, a type II transmembrane serine protease | unspecific, cleaves after Lys or Arg residues |
| Ovarian Cancer | MMP-2, MMP-9, kallikrein-10 (hk-10) | type IV and V collagens and gelatin, kininogens, plasminogen |
| Breast, gastric, prostate cancer | cathepsins B, L and D | broad spectrum of substrates |
| Endometrial cancer | cathepsin B | unspecific cleavage of a broad spectrum of substrates without clear sequence specificity |
| esophageal adenocarcinoma | cathepsin B | unspecific cleavage of a broad spectrum of substrates without clear sequence specificity |
| Invasive cancers, metastases | type II integral serine proteases (dipeptidyl peptidase IV (DPP4/CD26), seprase/fibroblast activation protein alpha (FAPalpha) and related type II transmembrane prolyl serine peptidases)) | |
| Invasive cancers, metastases | Seprase | various ECM proteins |
| Viral Infections | | |
| All Retroviruses | viral protease | precursor GagPol fusion |
| HIV | HIV protease (HIV PR, an aspartic protease) | precursor Gag and GagPol proteins |

TABLE 1-continued

Non-limiting examples of disease-associated enzymes and substrates.

| Disease | Enzyme | Substrate |
|---|---|---|
| Hepatitis C | NS3 serine protease | viral precursor polyprotein |
| Dengue | Dengue protease | autocleavage (NS2B/NS3), NS3/NS4A and NS4B/NS5 cleavage |
| West Nile | NS2B/NS3pro | viral precursor polyprotein |
| Bacterial Infections | | |
| *Legionella* spp. Meninogencephalitis | zinc metalloprotease histolytic cysteine protease | Me-Arg-Pro-Tyr |
| *Streptococcus pyogenes* (Group A *Streptococcus*) | streptococcal pyrogenic exotoxin B (SpeB) | extracellular matrix, immunoglobulins, complement components |
| *Clostridium difficile* | Cwp84 | fibronectin, laminin, vitronectin and other ECM proteins |
| *Pseudomonas aeruginosa* | lasA | Leu-Gly-Gly-Gly-Ala (SEQ ID NO: 1) |
| *Pseudomonas aeruginosa* | Large ExoProtease A | Cleavage of peptide ligands on PAR1, PAR2, PAR4 (Protease-activated receptor). See, e.g., Kida et al, Cell Microbiol. 2008 Jul; 10(7): 1491-504. |
| *Pseudomonas aeruginosa* | protease IV | complement factors, fibrinogen, plasminogen (See, e.g., Engel et al., J Biol Chem. 1998 Jul 3; 273(27): 16792-7). |
| *Pseudomonas aeruginosa* | alkaline protease | Complement factor C2 (See, e.g., Laarman et al., J Immunol. 2012 Jan 1; 188(1): 386-93). |
| Additional Diseases | | |
| Alzheimer's disease | BACE-1,2 (Alzheimer secretase) | β-amyloid precursor protein |
| Stroke and recovery | MMP, tPA | |
| cardiovascular disease | Angiotensin Converting Enzyme (ACE) | angiotensin I, bradykinin |
| Atherosclerosis | cathepsin K, L, S | broad spectrum of substrates |
| arthritis | MMP-1 | triple-helical fibrillar collagens |
| rheumatoid arthritis | thrombin | Osteopontin |
| Malaria | SUB1 | KITAQDDEES (SEQ ID NO: 2) |
| osteoarthritis | thrombin | Osteopontin |
| osteoporosis/osteoarthritis | cathepsin K, S | broad spectrum of substrates |
| Arthritis, inflammatory joint disease | Aggrecanase (ADAMTS4, ADAMTS11) | aggrecans (proteoglycans) |
| thrombosis | factor Xa (thrombokinase) | Prothrombin |
| thrombosis | ADAMTS13 | von Willebrand factor (vWF) |
| thrombosis | plasminogen activator, tPA | Plasminogen |
| Stress-induced Renal pressure natriuresis | Prostasin | epithelial Na channel subunits |

TABLE 2

Non-limiting examples of substrates associated with disease and other conditions.

| DISEASE | TARGET SUBSTRATE | ENZYME |
| --- | --- | --- |
| Inflammation | Interleukin 1 beta | MMP-2, MMP-3, MMP-9, Trypsin, chymotrypsin, pepsin, Lys-C, Glu-C, Asp-N, Arg-C |
| Pituitary gland dysfunction, abnormal bone density, growth disorders | IGFBP-3 | MMP-1, MMP-3, MMP-9, Trypsin, chymotrypsin, pepsin, Lys-C, Glu-C, Asp-N, Arg-C |
| Cancer | TGF-beta | MMP-9, Trypsin, chymotrypsin, pepsin, Lys-C, Glu-C, Asp-N, Arg-C |
| Cancer, autoimmune disease | TNF | MMP-7, Trypsin, chymotrypsin, pepsin, Lys-C, Glu-C, Asp-N, Arg-C |
| Cancer, autoimmune disease | FASL | MMP-7, Trypsin, chymotrypsin, pepsin, Lys-C, Glu-C, Asp-N, Arg-C |
| Wound healing, cardiac disease | HB-EGF | MMP-3, Trypsin, chymotrypsin, pepsin, Lys-C, Glu-C, Asp-N, Arg-C |
| Pfeiffer syndrome | FGFR1 | MMP-2, Trypsin, chymotrypsin, pepsin, Lys-C, Glu-C, Asp-N, Arg-C |
| Cancer | Decorin | MMP-2, MMP-3, MMP-7, Trypsin, chymotrypsin, pepsin, Lys-C, Glu-C, Asp-N, Arg-C |
| Cancer | Tumor associated carbohydrate antigens | Endoglycosidases |
| Cancer | Sialyl Lewis$^a$ | O-glycanase |
| Cancer | Sialyl Lewis$^x$ | O-glycanase |
| Cancer/Rheumatoid Arthritis, pulmonary hypertension | VEGF | Trypsin, chymotrypsin, pepsin, Lys-C, Glu-C, Asp-N, Arg-C |
| Cancer | EGF | Trypsin, chymotrypsin, pepsin, Lys-C, Glu-C, Asp-N, Arg-C |
| Cancer | IL2 | Trypsin, chymotrypsin, pepsin, Lys-C, Glu-C, Asp-N, Arg-C |
| Cancer inflammation/angiogenesis | IL6 | Trypsin, chymotrypsin, pepsin, Lys-C, Glu-C, Asp-N, Arg-C |
| Cancer | IFN-γ | Trypsin, chymotrypsin, pepsin, Lys-C, Glu-C, Asp-N, Arg-C |
| Cancer inflammation/angiogenesis, Rheumatoid Arthritis | TNF-α | Trypsin, chymotrypsin, pepsin, Lys-C, Glu-C, Asp-N, Arg-C |
| Cancer, Pulmonary fibrosis, Asthma | TGF-β | Trypsin, chymotrypsin, pepsin, Lys-C, Glu-C, Asp-N, Arg-C |
| Cancer, Pulmonary hypertension | PDGF | Trypsin, chymotrypsin, pepsin, Lys-C, Glu-C, Asp-N, Arg-C |
| Cancer, pulmonary cystadenoma | Fibroblast growth factor (FGF) | Trypsin, chymotrypsin, pepsin, Lys-C, Glu-C, Asp-N, Arg-C |
| Cancer | Brain-derived neurotrophic factor (BDNF) | Trypsin, chymotrypsin, pepsin, Lys-C, Glu-C, Asp-N, Arg-C |
| Cancer | Interferon regulatory factors (IRF-1, IRF-2) | Trypsin, chymotrypsin, pepsin, Lys-C, Glu-C, Asp-N, Arg-C |
| Inhibitor of tumor suppressors | MIF | Trypsin, chymotrypsin, pepsin, Lys-C, Glu-C, Asp-N, Arg-C |
| Lymphomas/carcinomas, alveolar proteinosis | GM-CSF | Trypsin, chymotrypsin, pepsin, Lys-C, Glu-C, Asp-N, Arg-C |
| Cancer invasion | M-CSF | Trypsin, chymotrypsin, pepsin, Lys-C, Glu-C, Asp-N, Arg-C |
| Chemical carcinogenesis, multiple sclerosis, rheumatoid arthritis, Crohn's disease | IL-12 | Trypsin, chymotrypsin, pepsin, Lys-C, Glu-C, Asp-N, Arg-C |
| Natural Killer T cell leukemias, inflammatory bowel disease, rheumatoid arthritis | IL-15 | Trypsin, chymotrypsin, pepsin, Lys-C, Glu-C, Asp-N, Arg-C |
| Cirrhosis | Tissue inhibitor of MMPs (TIMPs) | Trypsin, chymotrypsin, pepsin, Lys-C, Glu-C, Asp-N, Arg-C |
| Cirrhosis | Collagen I, III | MMP-1, MMP-8, Trypsin, chymotrypsin, pepsin, Lys-C, Glu-C, Asp-N, Arg-C |
| Cirrhosis | Collagen IV, V | MMP-2, Trypsin, chymotrypsin, pepsin, Lys-C, Glu-C, Asp-N, Arg-C |

For instance, a particular lung disease may be associated with a specific set of enzymes and the specific set of enzymes may distinguish one lung disease from another. Lung diseases include but are not limited to lung cancer, interstitial lung disease (ILD), and chronic obstructive pulmonary disease (COPD), and lung infections. The lung diseases may be primary or secondary diseases.

There are at least two types of lung cancer (e.g., non-small cell lung cancer (NSCLC) and small cell lung cancer (SCLC)). NSCLC accounts for about 85% of lung cancer cases and include adenocarcinoma, squamous cell carcinoma and large cell carcinoma. NSCLC may be characterized into stages I-IV by assessing the size and extent of the primary tumor, whether or not the cancer has spread to nearby lymph nodes and metastasis to distant sites (e.g., brain bones, kidneys, liver, or adrenal glands, or other lung). See, e.g., American Joint Committee on Cancer. Lung. In: AJCC Cancer Staging Manual. 8th ed. New York, N.Y.: Springer; 2017: 431-456. SCLC includes small cell carcinoma (oat cell cancer) and combined small cell carcinoma.

Interstitial lung disease (ILD) refers to disorders that cause fibrosis of the lungs. Non-limiting examples of ILDs include sarcoidosis, asbestosis, hypersensitivity pneumonitis, and idiopathic pulmonary fibrosis. In some cases, ILD is caused by exposure to hazardous chemicals, medical treatments, or medications.

Chronic obstructive pulmonary disease (COPD) may also be referred to as chronic bronchitis or emphysema. COPD is often characterized by obstructed airflow and difficulty breathing. Causes of COPD include tobacco smoke, air pollution and genetic alterations (e.g., alterations resulting in alpha 1 antitrypsin deficiency).

Infections or infectious diseases are diseases associated with an infectious agent (e.g., pathogens including bacteria, viruses, fungi, and protozoa). Non-limiting examples of pathogenic bacteria include *Streptococcus pneumoniae, Staphylococcus aureus, Streptococcus pygenes, Haemophilus influenza, Klebsiella pneumoniae, Escherichia coli, Pseudomonas aeruginosa, Mycoplasma pneumoniae, Legionella* spp, *Anaerobic bacteria, Mycobacterium tuberculosis, Mycoplasma* spp, *Coxiella burnelil, Chlamydia psittaci, Chlamydia trachomatis*, and *Chylamydia pneumoniae*. Non-limiting examples of viral pathogens include adenoviruses, influenza viruses, and respiratory syncytial viruses. Infections caused by pathogens include pneumonia and bronchitis. In some embodiments, an infection (e.g., an infection-specific) protease is an infectious agent-derived protease that is not present in a host (e.g., an infectious agent-specific protease). In some embodiments, an infection-specific protease is a protease that is not in healthy subjects or in samples from healthy subjects. In some embodiments, an infection-specific protease is a protease that is present in one type of infection but not in another type of infection. In some embodiments, an infection is a lung infection.

In some embodiments, an infection is associated with a virulence factor (e.g., a protease secreted by an infectious agent). In some embodiments, an infectious agent-specific (e.g., *Pseudomonas aeruginosa*-specific) protease is LasA (e.g., UniProtKB—Q02L18), Large ExoProtease A (LepA, e.g., UniProtKB—Q02L18), protease IV (e.g., UniProtKB—P08395), Protease IV, or alkaline protease (AprA, e.g., UniProtKB—Q4Z8K9). A non-limiting example of a LasA substrate is a sequence comprising the amino acid sequence LGGGA (SEQ ID NO: 1). See also FIG. 14.

In some embodiments, an infection is associated with a host factor (e.g., a protease secreted by an immune cells). For example, neutrophil elastase (ELA, e.g., NP_001963.1) is often secreted by neutrophils in response to an infection. A non-limiting example of a neutrophil elastase substrate includes AAFA (SEQ ID NO: 3) and Nle(O-Bzl)-Met(O)2-Oic-Abu (SEQ ID NO: 10). See, e.g., Kasperkiewicz, P. PNAS. 2014; 11(7): 2518-2523).

In some instances, a protease substrate comprises unnatural amino acids. Unnatural amino acids include 6-benzyloxynorleucine (Nle(O-Bzl)), methionine dioxide (Met(O) 2), octahydroindolecarboxylic acid (OIC); and α-aminobutyric acid (Abu).

A nanosensor may be designed with one or more substrates that match those of the enzymes expressed by diseased tissue (e.g., lung disease tissue). Alternatively, the substrate may be associated with enzymes that are ordinarily present but are absent in a particular disease state. In this example, a disease state would be associated with a lack of signal associated with the enzyme, or reduced levels of signal compared to a normal reference.

An enzyme, as used herein refers to any of numerous proteins produced in living cells that accelerate or catalyze the metabolic processes of an organism. Enzymes act on substrates and may be derived from a host or an infectious agent (e.g., pathogen associated with an infection). The substrate binds to the enzyme at a location called the active site just before the reaction catalyzed by the enzyme takes place. Enzymes include but are not limited to proteases, glycosidases, lipases, heparinases, phosphatases.

In some embodiments, a substrate comprises an amino acid sequence that is cleaved by an enzyme (e.g., a protease substrate). In some embodiments, the enzyme-specific substrate comprises an amino acid sequence cleaved by a serine protease, an alkaline protease, a lysine-specific protease, cysteine protease, threonine protease, aspartic protease (e.g., AspA), glutamic protease, and/or a metalloproteinase (i.e.: metalloprotease). As their names suggest, serine, cysteine, threonine, and aspartic proteases use a catalytic serine, cysteine, threonine, or aspartate residue, respectively, for catalysis. Mechanistically, metalloprotenaises use a metal in catalysis.

As used herein, a substrate (e.g., protease substrate) may be enzymatically cleaved by one or more proteases (e.g., at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 30, at least 40, at least 50, at least 60, or at least 100) proteases.

A nanosensor of the present disclosure may detect the activity of an endogenous and/or an exogenous protease. An endogenous protease is a protease that is naturally produced by a subject (e.g., subject with a particular disease or a host with a infection). An exogenous protease is a protease that is not naturally produced by a subject and may be produced by an infectious agent (e.g., a bacteria, a fungi, protozoa, or a virus). In some embodiments, a protease is only expressed by a subject (e.g., a human) and not by an infectious agent. In some embodiments, a protease is infectious agent-specific and is only produced by an infectious agent not by the infectious agent's host. Without being bound by a particular theory, a nanosensor that comprises a substrate for an infectious agent-specific protease would not be cleaved by a host-specific protease. In some embodiments, an infectious agent-specific protease is produced by one infectious agent but not another. Such infectious agent-specific proteases may be useful in distinguishing between different infectious agent-induced diseases. In some embodiments, a protease that is produced by a host, an infectious agent or both, but is not active does not promote the release of a detectable marker from a nanosensor.

A substrate may be attached directly to the scaffold. For instance it may be coated directly on the surface of microparticles using known techniques, or chemically bonded to a polymeric scaffold, such as a PEG scaffold (e.g., via a peptide bond). Additionally, the substrate may be connected to the scaffold through the use of a linker. As used herein "linked" or "linkage" means two entities are bound to one another by any physicochemical means. Any linkage known to those of ordinary skill in the art, covalent or non-covalent, is embraced. Thus, in some embodiments the scaffold has a linker attached to an external surface, which can be used to link the substrate. Another molecule can also be attached to the linker. In some embodiments, two molecules are linked using a transpeptidase, for example Sortase A.

Examples of linking molecules include but are not limited to poly(ethylene glycol), peptide linkers, N-(2-Hydroxypropyl) methacrylamide linkers, elastin-like polymer linkers, and other polymeric linkages. Generally, a linking molecule is a polymer and may comprise between about 2 and 200 (e.g., any integer between 2 and 200, inclusive) molecules. In some embodiments, a linking molecule comprises one or more poly(ethylene glycol) (PEG) molecules. In some embodiments, a linking molecule comprises between 2 and 200 (e.g., any integer between 2 and 200, inclusive) PEG molecules. In some embodiments, a linking molecule comprises between 2 and 20 PEG molecules. In some embodiments, a linking molecule comprises between 5 and 15 PEG molecules. In some embodiments, a linking molecule comprises between 5 and 25 PEG molecules. In some embodiments, a linking molecule comprises between 10 and 40 PEG molecules. In some embodiments, a linking molecule comprises between 25 and 50 PEG molecules. In some embodiments, a linking molecule comprises between 100 and 200 PEG molecules.

The substrate is preferably a polymer made up of a plurality of chemical units. A "chemical unit" as used herein is a building block or monomer which may be linked directly or indirectly to other building blocks or monomers to form a polymer (e.g., a multi-arm PEG scaffold).

Methods of Detecting Enzyme Activity

Compositions (e.g., nanosensors) described herein can be administered to any suitable subject. As used herein, a subject is a human, non-human primate, cow, horse, pig, sheep, goat, dog, cat, or rodent. The subject may have, be at risk for, or is suspected of having a disease (e.g., an infectious disease, cancer, inflammation and/or a lung disease).

The enzyme nanosensors of the disclosure are administered to the subject in an effective amount for detecting enzyme activity. An "effective amount", for instance, is an amount necessary or sufficient to cause release of a detectable level of volatile reporter in the presence of an enzyme. The effective amount of a composition described herein may vary depending upon the specific composition used, the mode of delivery of the composition, and whether it is used alone or in combination with other compounds (e.g., a composition comprising a multiplexed library of nanosensors or combined with administration of a therapeutic agent). The effective amount for any particular application can also vary depending on such factors as the disease being assessed or treated, the particular compound being administered, the size of the subject, or the severity of the disease or condition as well as the detection method. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective regimen can be planned.

Pharmaceutical compositions of the disclosure comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated. The agent may comprise different types of carriers depending on whether it is to be administered in solid, liquid or aerosol form, and whether it need to be sterile for such routes of administration as injection.

Any suitable route of administration may be used. In some instances, the nanosensor is administered through inhalation. In some instances, the nanosensor is administered intravenously, intranasally, subcutaneously, or any combination thereof.

Any suitable method known in the art or disclosed herein may be used to detect a volatile reporter (e.g., synthetic volatile reporter) that has been released from the nanosensor. As a non-limiting example, a biological sample (e.g., breath sample, blood sample, feces sample, urine sample, sputum sample, sweat sample) may be collected from a subject who has been administered a nanosensor of the present disclosure and the biological sample may be assayed to detect a released volatile reporter. In some instances, the biological sample is a blood culture, a sputum culture, or a combination thereof. In some instances, the level of a released volatile reporter in a sample obtained from a subject who has been administered a nanosensor is compared relative to the level of the endogenous levels of the released volatile reporter. In some instances, an increase in the presence of the volatile reporter relative to the level of the volatile reporter from a healthy subject is indicative of the subject having a disease. In some instances, the presence of a released synthetic volatile reporter in a biological sample obtained from a subject who has been administered a nanosensor is indicative of the subject having a disease.

EXAMPLES

In the proof-of-concept experiments described herein, neutrophil elastase (NE) was chosen as an initial target due to the availability of an optimized neutrophil elastase substrate with a cleavage site after the C-terminal residue (see, e.g., Kasperkiewicz et al., PNAS 111, 2518-2523 (2014)), significant neutrophil presence in bacterial pneumonia models already established in the lab, and high micromolar concentration of neutrophil elastase in the extracellular environment upon release from neutrophils (see, e.g., Liou et al., Biochemistry 34, 16171-16177 (1995)).

Figure 2C:
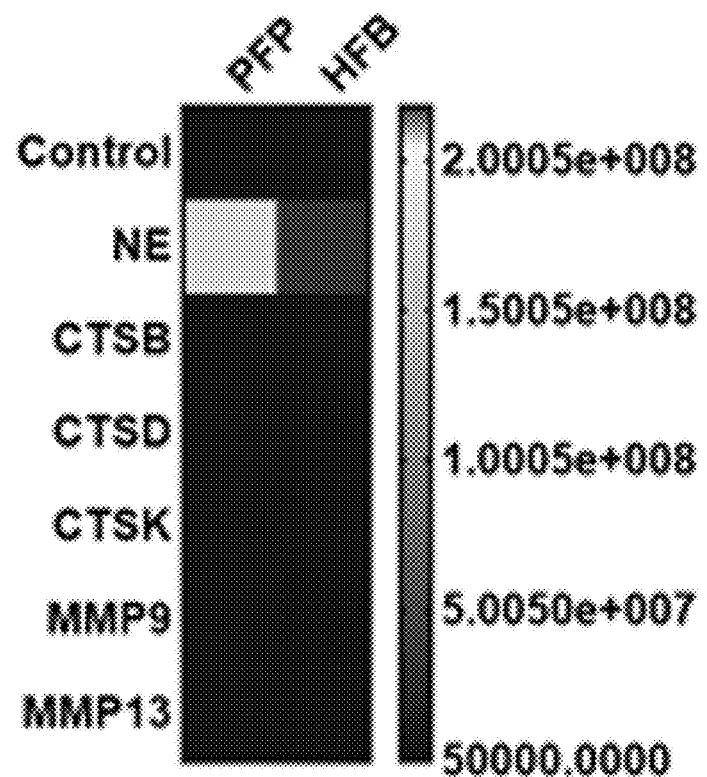
Figure 2D:
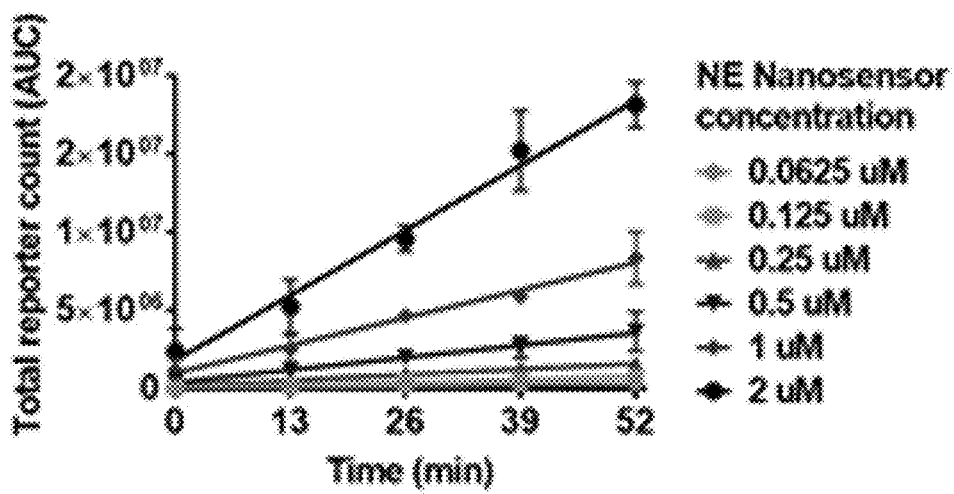

To assemble the NE nanosensor, the NE peptide substrate (Nle(O-Bzl)Met(O)2-Oic-Abu (see, e.g., Kasperkiewicz et al., PNAS 111, 2518-2523 (2014))) was first synthesized with the following modifications using solid phase peptide synthesis: (1) an acetylated N-terminal CKKK-PEG$_4$ (SEQ ID NO: 4) linker for conjugation to a maleimide-functionalized 8-arm PEG and (2) a C-terminal PFC reporter (pentafluoropropylamine or heptafluorobutylamine). PFC release from the peptide substrate was measured using a real-time vapor analysis mass-spectrometer. Both peptide-PFCs were stable in solution and cleaved specifically by NE with minimal cleavage by other proteases found in the respiratory tract (cathepsins (see, e.g., Meyer et al., Am J Physiol Lung Cell Mol Physiol 308, L1189-L1201 (2015)) and proteases upregulated in other respiratory diseases such as lung adenocarcinoma (MMP9 and MMP13 (see, e.g., Salaun et al., PLoS One 10, e0132960 (2015); El-Badrawy et al., J Bronchol. Interv Pulmonol 21, 327-334 (2014)) (FIG. 2C). Both peptide-PFCs were conjugated to a 40 kDa 8-arm PEG scaffold, which prevents the low molecular weight substrate-reporter constructs from entering systemic circulation, thus, enabling retention in the lung after inhalation. Reporter release from the completed nanosensors were measured during time-lapsed studies to derive Michaelis-Menten kinetics of substrate cleavage (FIG. 2D). $k_{cat}/K_m$ values were on the order of $10^5$ $M^{-1}s^{-1}$ for heptafluorobutyllamine and pentafluoropropylamine, respectively.

Figure 3A:
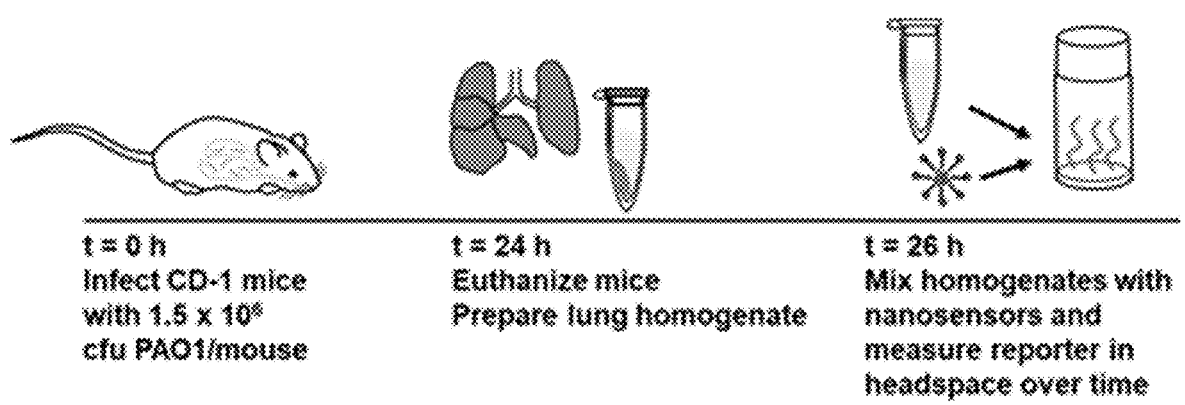
FIGS. 3A-3C show that NE nanosensors release volatile reporters in lung homogenates from mice with bacterial pneumonia.
Figure 3B:
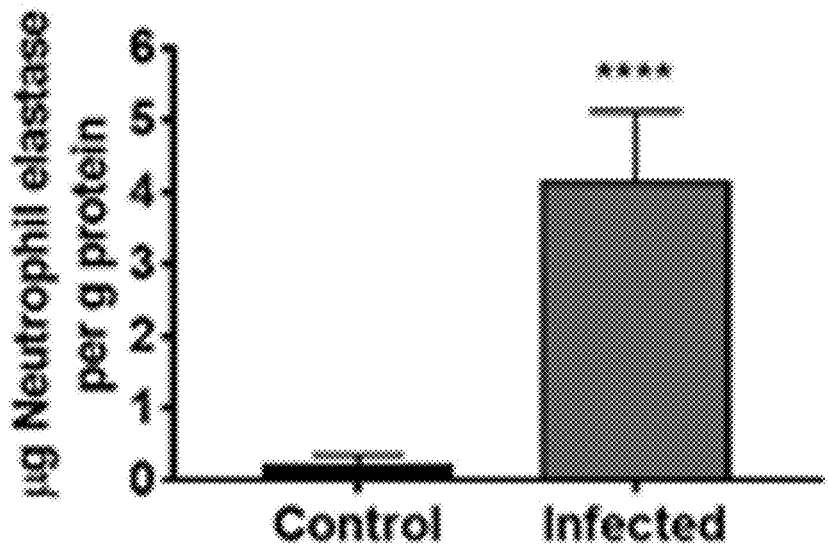
Figure 3C:
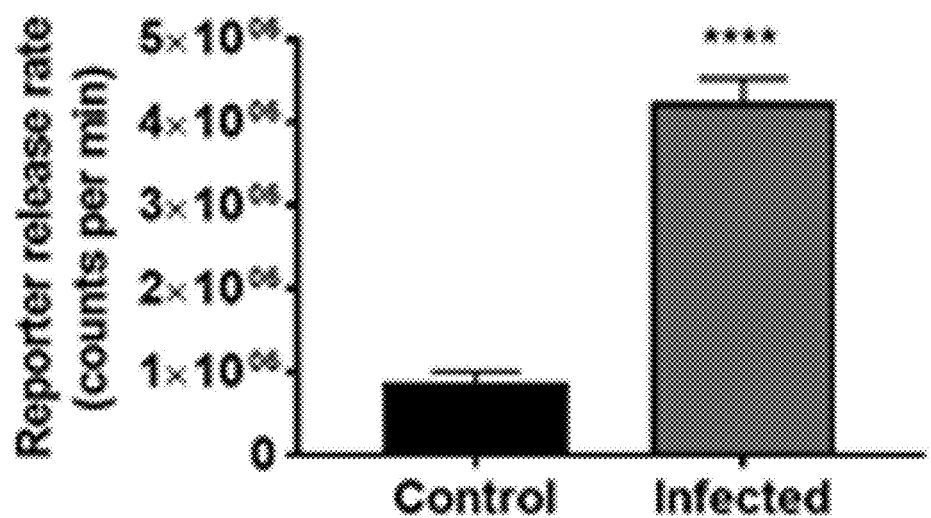
Figure 7:
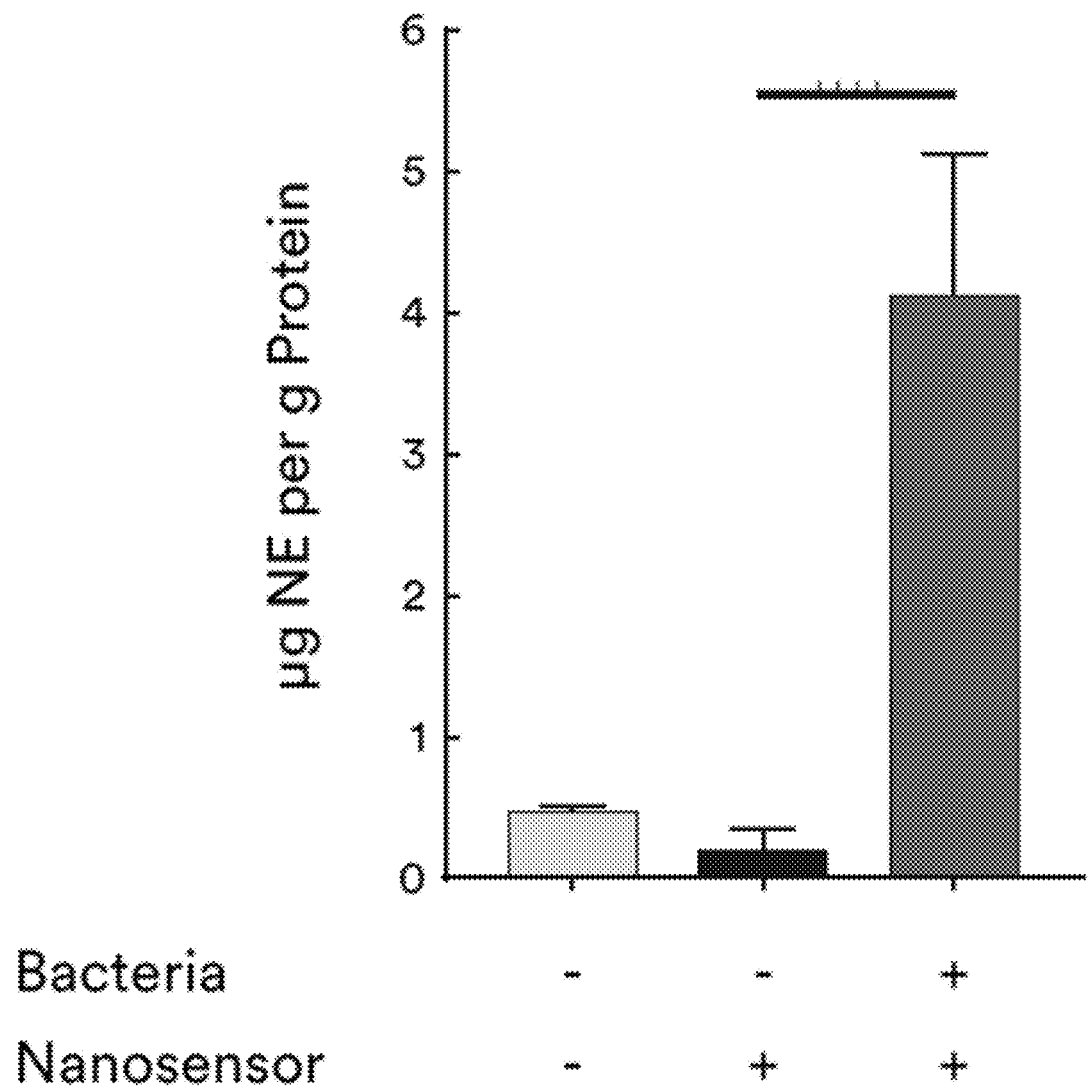
FIG. 7 shows the results of a study to detect neutrophil elastase quantification. Reporter levels are 3-fold greater in infected breath than in healthy breath 18 min after nanosensor inhalation ($p=0.0035$). ELISA assay confirms higher NE concentration in infected mouse lungs.

Ultimately, the goal was to administer nanosensors into the lungs of mouse models of bacterial pneumonia to test for measurable reporter levels in the breath. Prior to direct administration into animal infection models, nanosensors were mixed ex vivo with infected and healthy lung homogenates. Bacterial pneumonia was established in CD-1 mice by intratracheal injection of $1.5 \times 10^6$ cfu *Pseudomonas aeruginosa* strain PAO1 (FIG. 3A). At 24 h post-inoculation, the time at which mice were euthanized and lung homogenates were prepared, infected lung homogenates had ~22-fold greater neutrophil elastase concentration than healthy lung homogenates (FIG. 3B and FIG. 7). Intracellular and secreted NE, both proteolytically active as well as inactive pro-forms, likely contribute to the total amount of NE measured by ELISA. When mixed with nanosensors, infected lung homogenates triggered 5-fold faster reporter release compared to healthy lung homogenates (FIG. 3C).

Figure 4A:
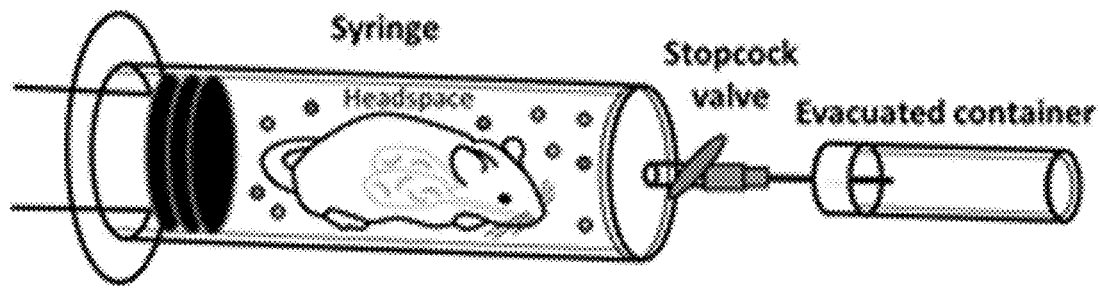
FIGS. 4A-4E include data showing that NE nanosensors release measurable levels of reporters into the breath for differentiation between healthy controls and mice with bacterial pneumonia.
Figure 4B:
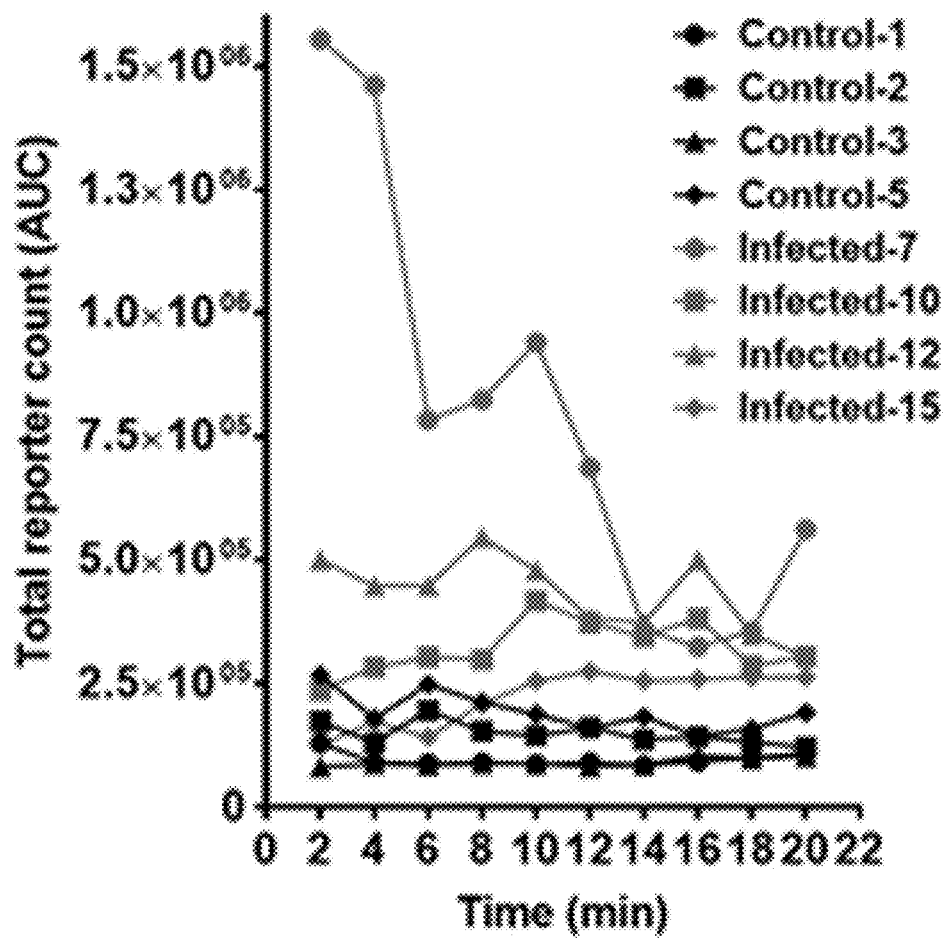
Figure 4C:
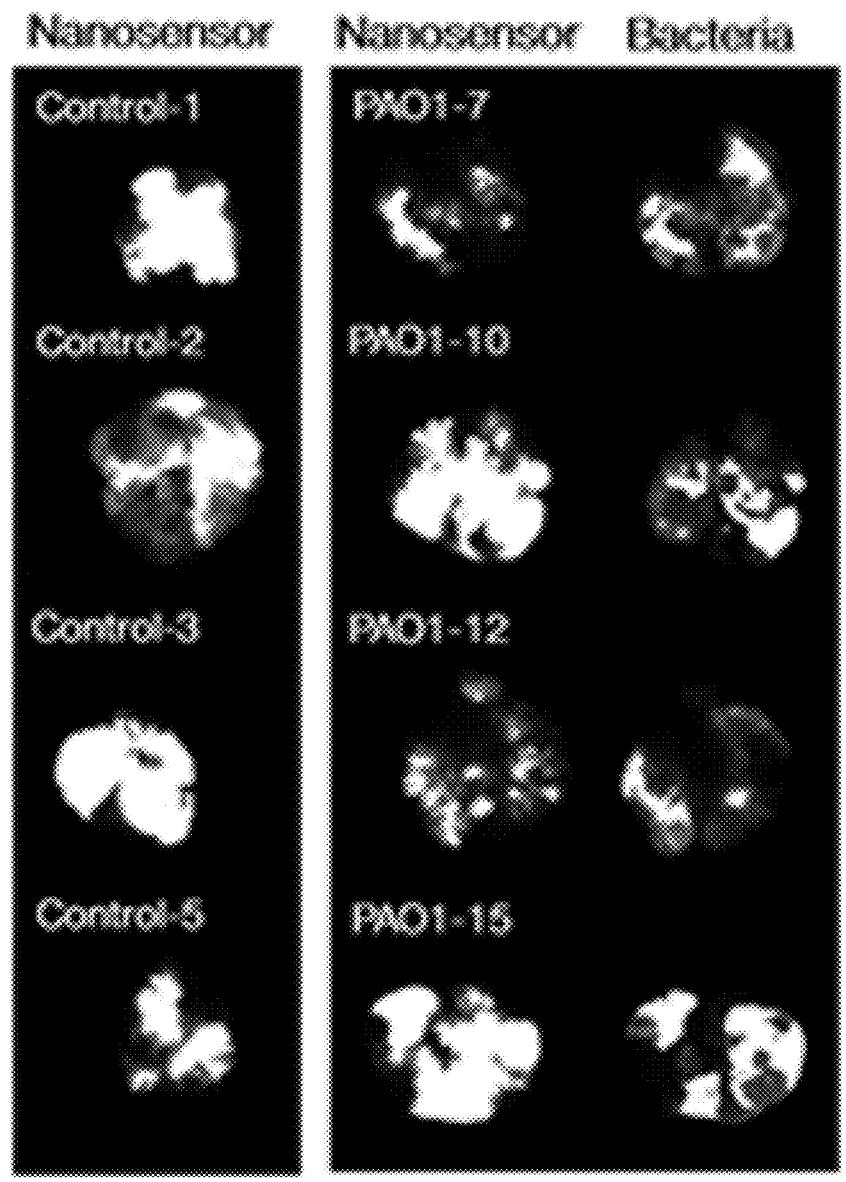
Figure 4D:
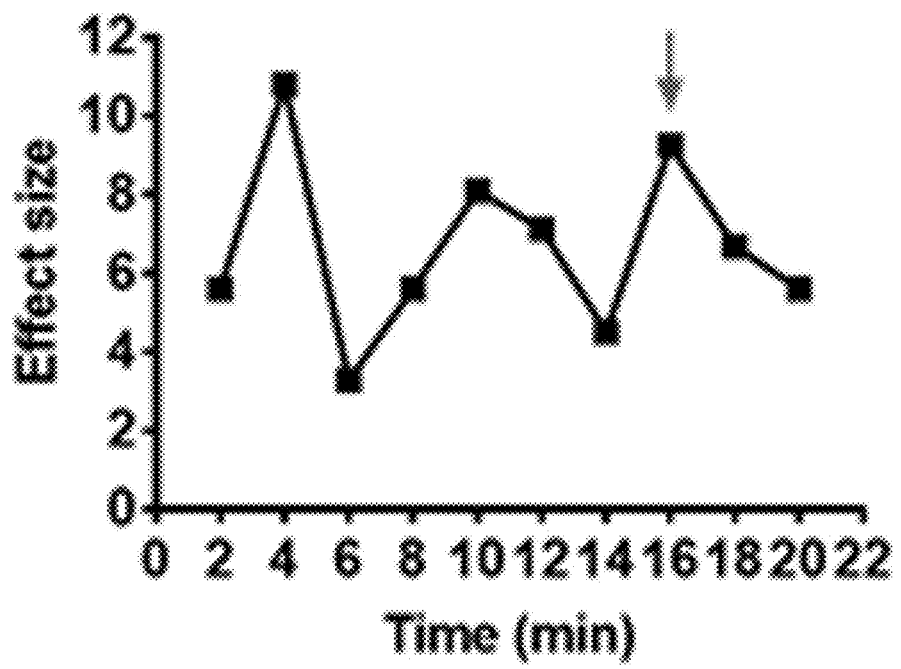
Figure 4E:
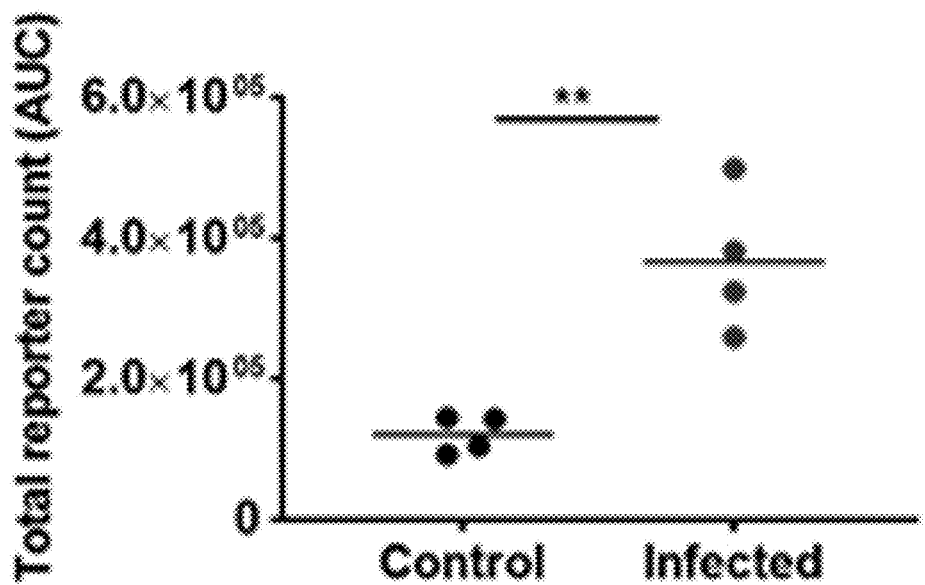
Figure 5:
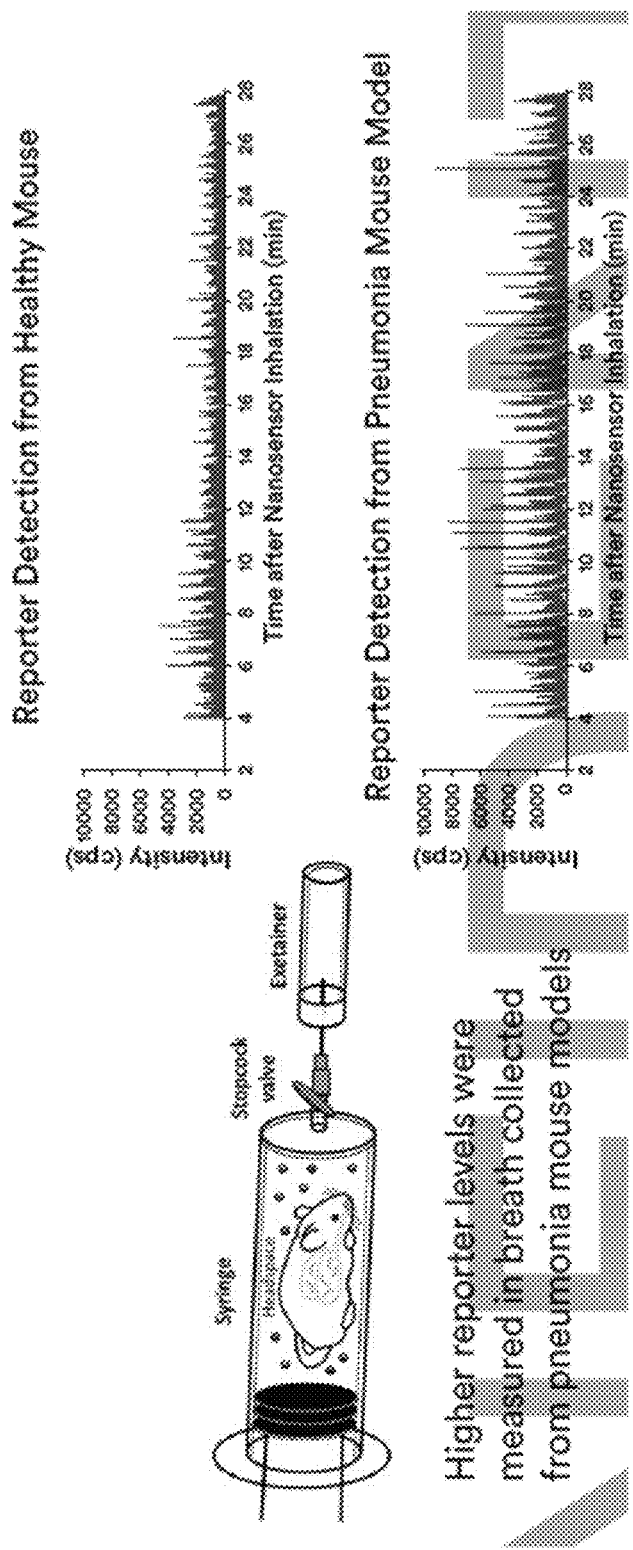
FIG. 5 shows a non-limiting example of an in vivo test on mouse breath. Reporter detection from healthy mouse and reporter detection from pneumonia mouse model were examined. Higher reporter levels were measured in breath collected from pneumonia mouse models.
Figure 6:
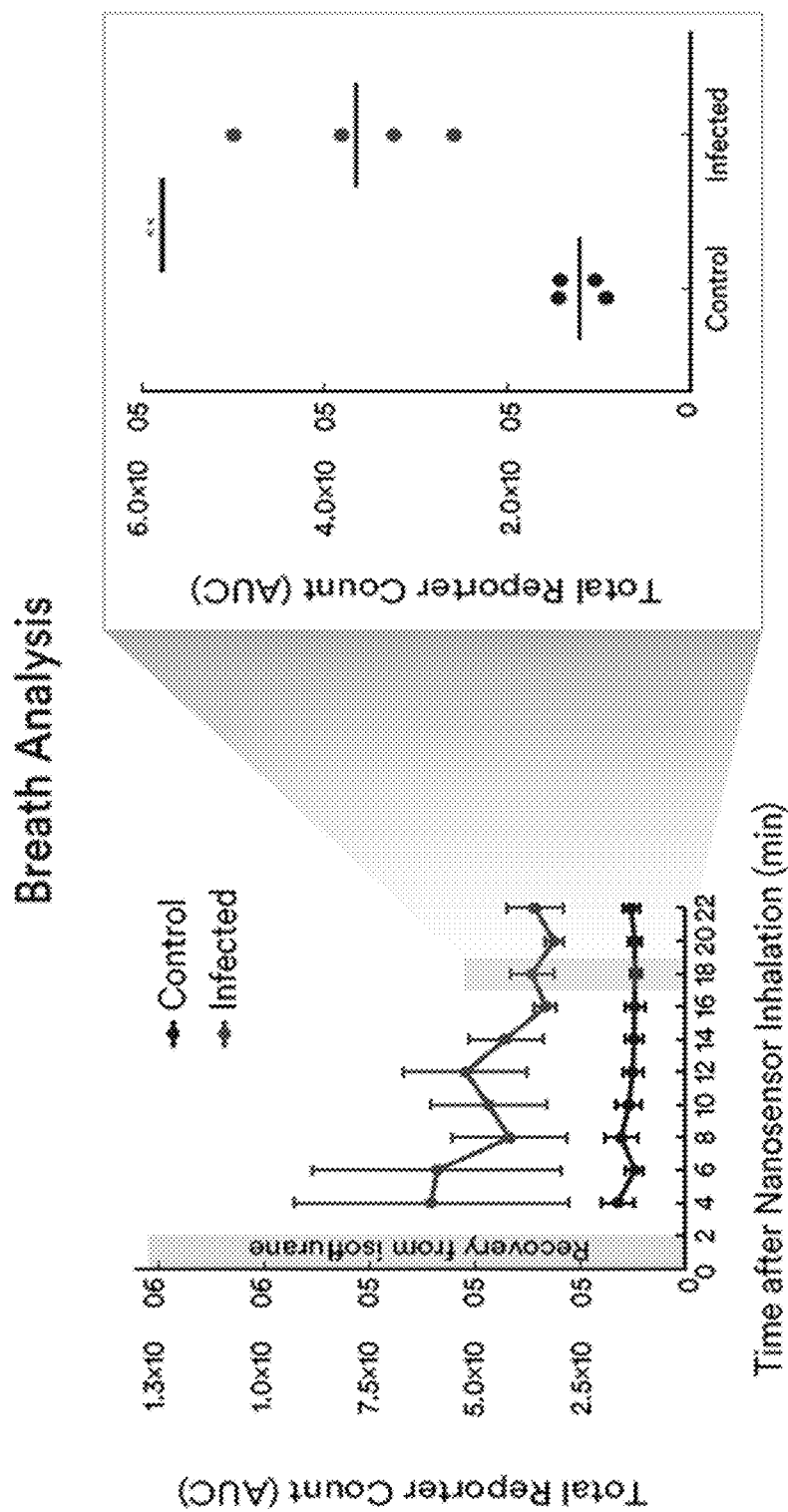
FIG. 6 includes data showing that a nanosensor could be used to differentiate healthy and infected mice.

With confirmation that infected lungs trigger greater reporter release and at detectable levels, nanosensors were then tested in acute pneumonia mouse models. 24 h post-infection with *P. aeruginosa* (strain PAO1), a nanosensor dose with either 500 pmol or 5 nmol equivalence of pentafluoropropylamine reporter (10 or 100 µM concentration) was administered into mice via intratracheal injection. 2 min after nanosensor administration, breath was collected at 2, 4, 6, 8, 10, 20, 30, and 60 min in evacuated 12 cc EXETAINER™ tubes (Labco) (FIG. 4A and FIG. 5). Reporter levels in the breath of healthy controls were consistently low over time, while reporter levels in the breath of infected mice showed some variability in the first 14 min of breath collection and then converged at levels ~3-fold greater than healthy controls (FIG. 4B and FIG. 6, left). The initial variability might be explained by nanosensor distribution in the lung, as shown in Licor images of signal from Cy5-labeled nanosensors (FIG. 4C). Infected-7 and Infected-12, which have high initial reporter levels, have nanosensors predominantly in the airway. In contrast, Infected-10 and Infected-15, with low initial reporter levels, have dispersed nanosensor distribution deep in the lung. Reporters released from the sensor in the airways are expected to be expired in the breath more rapidly than free reporters deeper in the lung as the tidal volume is only a fraction of the total volume of the lung. Nevertheless, reporter levels converge after 14 min and a 2-way ANOVA indicates that reporter levels are significantly greater in infected mice than healthy controls (p<0.05). The maximum effect size of reporter levels at 16 min indicates that breath may be collected at this timepoint and analyzed for classification of healthy and infected mice (FIG. 4D). In fact, infected breath samples at 16 min (18 min post-injection) have 3-fold higher mean reporter levels than breath samples from healthy controls (p=0.0035) (FIG. 4E and FIG. 6, right).

Figure 8:
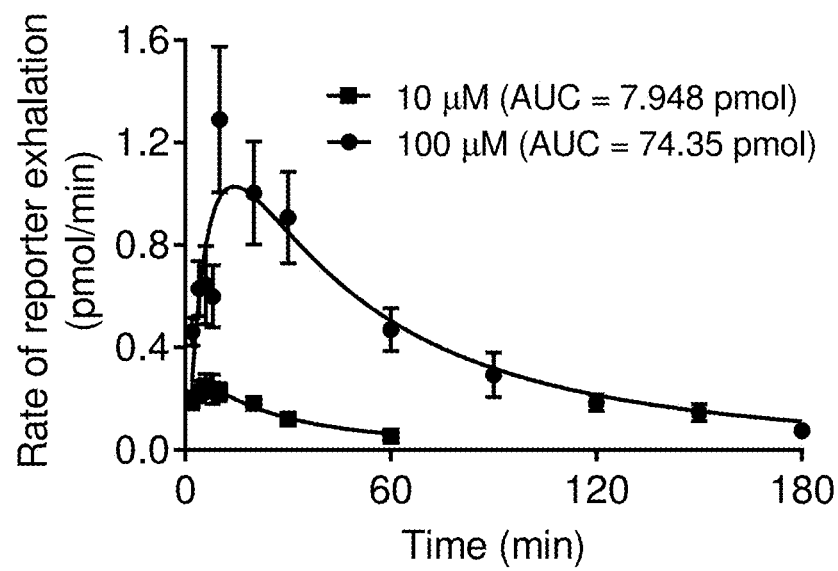
FIG. 8 shows rate of reporter exhalation after nanosensor administration in P. aeruginosa-infected mice for 10 and 100 µM doses. In pneumonia mouse models, reporter levels in breath were detectable after intratracheal instillation of a 10 µM equivalent peptide dose. Breath signal peaked by 10 min and declined back to baseline by 1 h and 3 h for 10 µM and 100 µM doses, a first indicator that reporters in breath might provide a rapid readout
Figure 9:
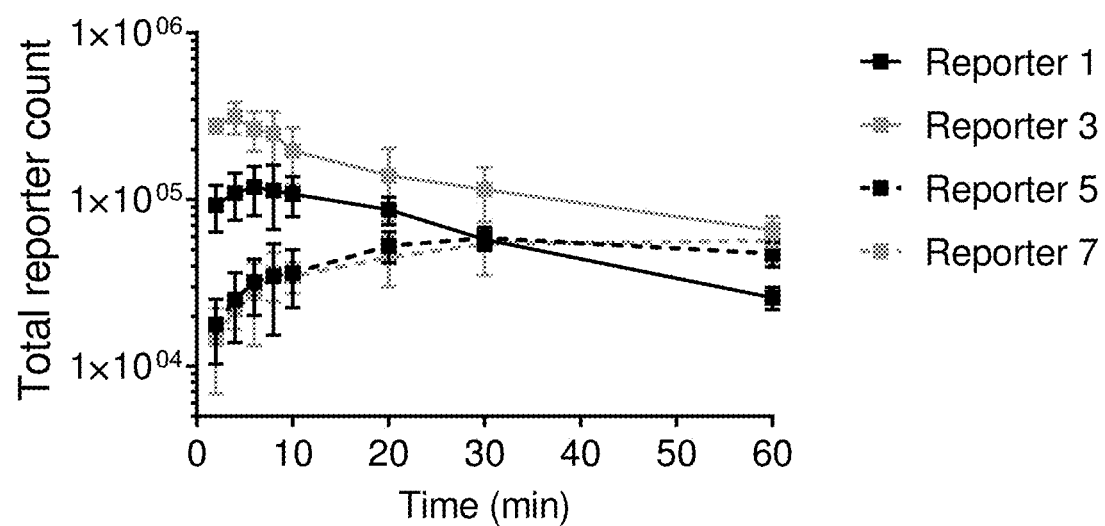
FIG. 9 shows that increasing the length of the perfluorcarbon reporter can slow down breath signal kinetics.
Figure 10A:
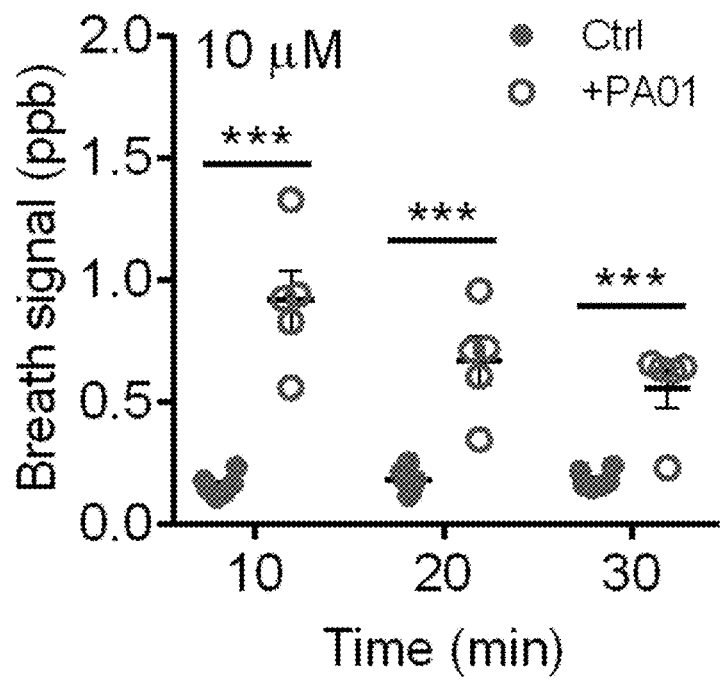
FIG. 10A shows results with 10 µM dose.
Figure 10B:
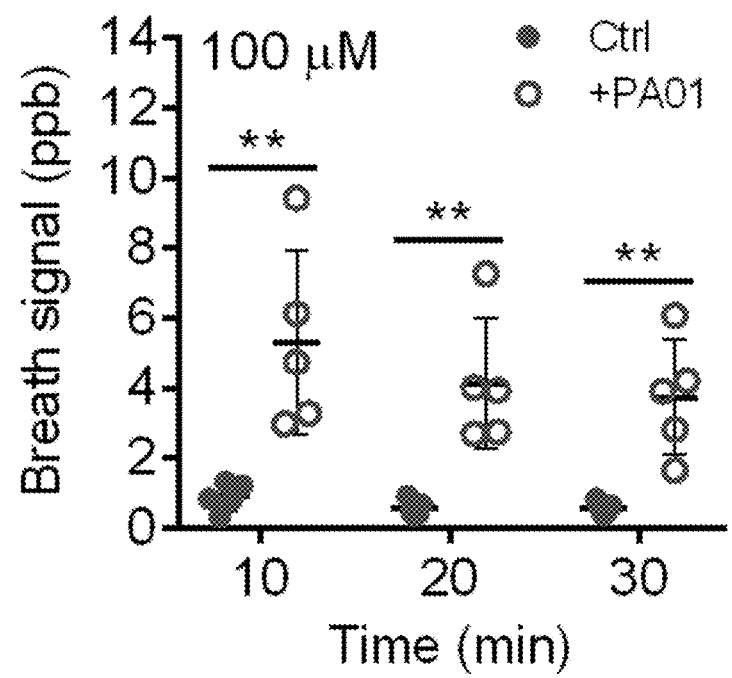
FIG. 10B shows results with 100 µM dose.
Figure 10C:
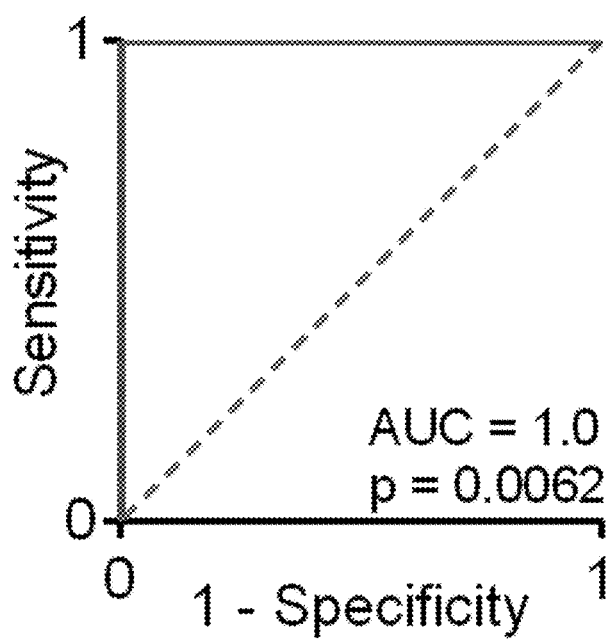
Figure 11A:
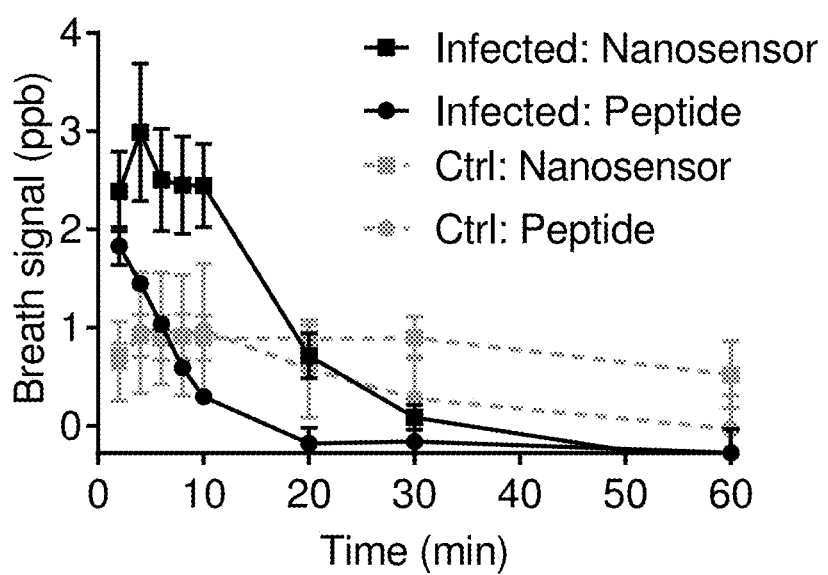
FIGS. 11A-11B show the superior effects of the nanoparticle scaffold on breath signal as compared to the effect of peptide substrate unattached to a nanoparticle scaffold on breath signal.
Figure 11B:
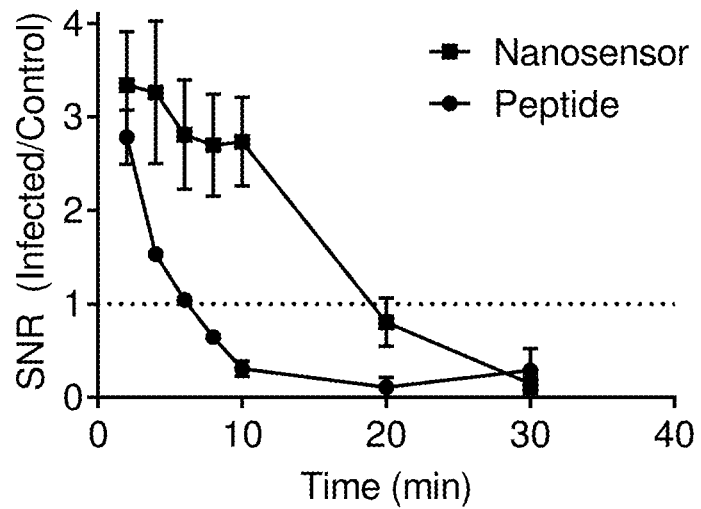
Figure 12:
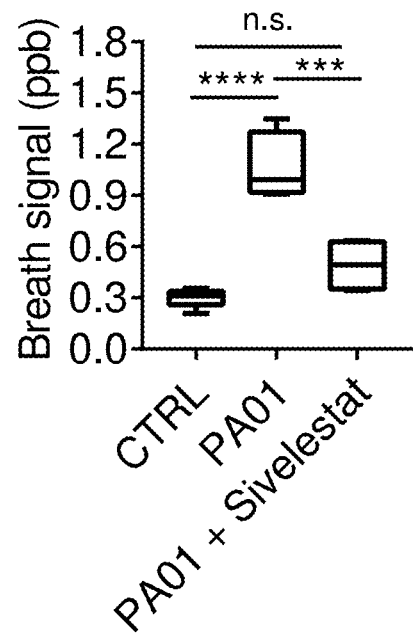
FIG. 12 is a graph showing the role of neutrophil elastase (NE) in releasing reporters in vivo to generate breath signal. Sivelestat is a small molecule inhibitor of NE.

Reporter concentrations in breath samples were measured using a real-time vapor analysis mass spectrometer and the resulting time versus breath signal curves reflect rapid reporter release and reporter clearance from the lung for both nanosensor doses (FIG. 8). Breath signal was observed to be dose-dependent, peaked by 10 min, and returned back to baseline at ~1 and ~3 hr for the low and high dose, respectively. A follow-up experiment using the same animal model and low nanosensor dose demonstrated that increasing the length of the perfluorcarbon reporter can slow down breath signal kinetics (FIG. 9). Therefore, subsequent studies focused on nanosensors with pentafluoropropylamine or heptafluoropropylamine reporters. To determine if breath signal could be used to identify infected mice based on elevated NE levels, breath was collected from healthy and infected mice after administration of low and high dose nanosensor. Breath signal was significantly higher in infected mice at 10, 20, and 30 min after nanosensor administration for both low and high nanosensor doses (FIGS. 10A-10B). Using breath signal at 10 min for the low nanosensor dose, infected mice could be identified with high sensitivity and specificity (AUROC=1.0, p=0.0062, FIG. 10C). To determine the effect of the nanoparticle scaffold on breath signal, control and infected mice were dosed with nanosensor or peptide substrate unattached to a nanoparticle scaffold. Nanosensors produced higher breath signal than peptide substrates in infected mice (FIG. 11A) and SNR was maintained at >1.0 for ~3× longer (FIG. 11B). In a subsequent mechanistic study, a small molecule inhibitor for NE, sivelestat, was administered via intratracheal injection at a 5 mg/kg dose in infected mice 15 min before nanosensor administration. Breath signal was reduced by ~70% due to inhibitor administration, confirming the role of NE in releasing reporters in vivo to generate breath signal (FIG. 12).

Therefore, a nanosensor comprising a synthetic volatile reporter and an enzymatic substrate could be used to detect in vivo NE activity and could be used to distinguish between subjects with an infection and healthy subjects.

What is claimed is:

1. A nanosensor comprising a scaffold linked to a synthetic volatile reporter via an enzymatic substrate, wherein the volatile reporter is capable of being released from the nanosensor when exposed to an enzyme present in a lung of a subject.

2. The nanosensor of claim 1, wherein the scaffold comprises a biological macromolecule, a synthetic macromolecule, or a particle.

3. The nanosensor of claim 2, wherein the biological macromolecule is a protein, lipid, carbohydrate, or a nucleic acid.

4. The nanosensor of claim 2, wherein the synthetic macromolecule is a synthetic polymer.

5. The nanosensor of claim 2, wherein the particle is a nanoparticle or a microparticle.

6. The nanosensor of claim 2, wherein the scaffold has total molecular weight greater than 40 kDa.

7. The nanosensor of claim 2, wherein the synthetic volatile reporter comprises at least one perfluorocarbon.

8. The nanosensor of claim 7, wherein the perfluorocarbon has the chemical formula $CF_3(CF_2)_xCH_2NH_2$, wherein x is a number in a range of 1 to 100.

9. The nanosensor of claim 1, wherein the scaffold comprises a multi-arm polyethylene glycol molecule (multi-arm PEG).

10. The nanosensor of claim 9, wherein the multi-arm PEG has a total molecular weight greater than 40 kDa.

11. The nanosensor of claim 1 or 2, wherein the scaffold is linked to a single enzymatic substrate.

12. The nanosensor of claim 1, wherein the enzymatic substrate comprises an infectious agent substrate.

13. A method comprising:
(a) detecting in a breath sample obtained from a subject that has been administered one or more nanosensors of claim 12 one or more volatile reporters that have been released from the one or more nanosensors when exposed to the enzyme present in the lung of the subject; and
(b) classifying the subject as having an infection upon detection of the one or more volatile reporters.

14. The nanosensor of claim 12, wherein the enzymatic substrate is cleaved by an enzyme associated with an infection in a subject.

15. The nanosensor of claim 1, wherein the scaffold is linked to a single volatile reporter.

16. The nanosensor of claim 1, wherein the scaffold is linked to multiple volatile reporters via one or more enzymatic substrates.

17. The nanosensor of claim 1, wherein the scaffold is linked to 2 to 20 different enzymatic substrates.

18. The nanosensor of claim 1, wherein the enzymatic substrate is a peptide, a nucleic acid, a glycan, or a lipid.

19. The nanosensor of claim 1, wherein the synthetic volatile reporter comprises at least one perfluorocarbon.

20. The nanosensor of claim 19, wherein the perfluorocarbon has the chemical formula $CF_3(CF_2)_xCH_2NH_2$, wherein x is a number in a range of 1 to 100.

21. The nanosensor of claim 20, wherein the perfluorocarbon is pentafluoropropylamine or heptafluorobutylamine.

22. A method comprising detecting in a breath sample obtained from a subject that has been administered one or more nanosensors of claim 1 one or more volatile reporters that have been released from the one or more nanosensors when exposed to the enzyme present in the lung of the subject.

23. The method of claim 22, wherein the detecting comprises mass spectrometry, ion mobility spectroscopy, or any combination thereof.

24. The method of claim 22, wherein the administration of the one or more nanosensors is by inhalation.

25. A method comprising:
(a) administering one or more nanosensors of claim 1 to a subject; and
(b) detecting in a breath sample obtained from the subject one or more volatile reporters that have been released from the one or more nanosensors when exposed to the enzyme present in the lung of the subject.

26. The method of claim 25, wherein the subject has, is suspected of having, or is at risk for an infectious disease.

27. The method of claim 26, wherein the subject has, is suspected of having, or is at risk for pneumonia.

28. The method of claim 25, wherein an increase in the presence of the one or more volatile reporters relative to a level of the one or more volatile reporters from a healthy subject is indicative of the subject having a disease.

* * * * *